United States Patent
Beaudry et al.

[11] Patent Number: 5,822,068
[45] Date of Patent: Oct. 13, 1998

[54] NON-DESTRUCTIVE METHOD AND APPARATUS FOR DETECTION OF FRUIT AND VEGETABLE QUALITY

[75] Inventors: Randolph M. Beaudry, East Lansing, Mich.; Paul R. Armstrong, Stillwater, Okla.; Jun Song; Weimin Deng, both of East Lansing, Mich.

[73] Assignee: Board of Trustees operating Michigan State University, East Lansing, Mich.

[21] Appl. No.: 815,115

[22] Filed: Mar. 10, 1997

[51] Int. Cl.⁶ ........................................... G01N 21/64
[52] U.S. Cl. .................... 356/417; 356/318; 250/458.1
[58] Field of Search .................... 356/317, 318, 356/417; 250/458.1, 459.1, 910

[56] References Cited

U.S. PATENT DOCUMENTS

| | | |
|---|---|---|
| 2,933,613 | 4/1960 | Powers . |
| 3,773,172 | 11/1973 | McClure et al. . |
| 3,930,994 | 1/1976 | Conway et al. . |
| 3,980,181 | 9/1976 | Hoover et al. . |
| 3,998,555 | 12/1976 | Hanscom et al. . |
| 4,106,628 | 8/1978 | Warkentin et al. . |
| 4,132,314 | 1/1979 | Von Beckmann et al. . |
| 4,170,306 | 10/1979 | Marshall et al. . |
| 4,205,752 | 6/1980 | Malwick et al. . |
| 4,281,933 | 8/1981 | Houston et al. . |
| 4,330,062 | 5/1982 | Conway et al. . |
| 4,476,982 | 10/1984 | Paddock et al. . |
| 4,558,786 | 12/1985 | Lane . |
| 5,401,954 | 3/1995 | Richert . |

FOREIGN PATENT DOCUMENTS 63-246639  10/1988  Japan .

OTHER PUBLICATIONS

Dull, G. G., et al., Quality In: A.C. Hulme (ed.) The biochemistry of fruit and their Products. vol. 2, 721–725 (1971).
Lovelidge, B., et al., Grower 108:53–54 (1987).
Abbott, J.A., et al., Food Technol. 22:101–112 (1968).
Abbott, J.A., et al., J. Amer. Soc. Hort. Sci. 117:590–595 (1992).
Armstrong, P.R., et al., Transactions of the ASAE 33:1353–1359 (1990).
Liljedahl, L. A., and J. A. Abbott, Trans. ADAE (1994).
Mishra, P.K. and G.S. Singhal, Plant Phys. 98:1–6 (1992).
VanKooten, O., et al., Photosyn. Res. 25:147–150 (1990).
Schreiber, U., and W. Bilger, Progress in Botany 54:151–173 (1993).
Havaux, M., et al., Planta 186:88–89 (1991).
Smillie,R.M., et al., Asean Fd. J. 3:55–59 (1987).
DeEll, J.R., et al., HortScience 30:782 (1995).
Beaudry, R., et al., HortScience 30:816 (1995).
Meir, S., et al., Postharvest biol. Tech. 2:125–135 (1992).
Thompson,J.E., The molecular basis for membrane deterioration during senescence.In.L.D. Nooden and A.C.Leopold (eds.). 51–83 (1988).
Gepstein,S., Photsynthesis.In:L.D.Nooden and A. C.Leopold (eds) Senescence and aging in plants. Academic press, NY. pp. 85–109 (1988).
Giersch, C., et al., Photosyn. Res. 30:115–121 (1991).
Hariyadi,P., et al., Postharvest Biol. Technol. 1:33–45 (1991).

(List continued on next page.)

*Primary Examiner*—F. L. Evans
*Attorney, Agent, or Firm*—Ian C. McLeod

[57] ABSTRACT

A non-destructive method of testing of fruits and vegetables for post-harvest quality (firmness, texture, aroma and color) using fluorescence intensity of the skin or leaves is described. A low intensity red light source (10) is used to irradiate the skin or leaves of fruits or vegetables to provide a first level $F_o$ of fluorescence intensity above that of red light in the 710 to 740 nM range. A second high intensity red light source is used to produce a maximal second fluorescence intensity $F_m$ in the skin or leaves in the 710 to 740 nM range. The ratio $F_v/F_m = (F_m - F_o)/F_m$ is then preferably determined to provide a measure of the quality of the fruit or vegetable.

24 Claims, 18 Drawing Sheets

OTHER PUBLICATIONS

Brown, G.K., and Y. Saring. ASAE May 1994. Nondestr. Tech. for Quality Evaluation of Fruits and Veg. pp. 120–147.Amer.Soc.Ag.Eng.St.Joseph MI (1994).

Mir, N.A., et al., Plant Physiol 108:313–318 (1995).

Brackman, A.J., et al., J.Amer.Soc.Hort. Sci. 118:243–247 (1993).

Knee, M., et al., J. Hort. Sci. 64:403–411 (1989).

Lau, O.L., Harvest indices for B.C. apples. B.C. Orchardist 7:1A–20A (1985.

Lau, O.L., J. Amer. Soc. Hort. Sci. 113:564–569 (1988).

Kingston, C.M., Horticulture Review, 407–432 (1992).

Knee, M., J. Expt. Bot. 23:184–196 (1972).

Abbott,J.A., ASAE May 1994 (1994).

Woolf, A.B., and W.A. Laing, J. Amer. Soc. Hort. Sci. 121:147–151 (1996).

Watkins, C.B., et al., J. Amer. Soc. Hort Sci. 120:88–94 (1995).

Wilson and Greaves, chilling Injury in Horticultural Scrops, ed. C.Y. Wang (1990).

Schreiber et al., Photosynth Res 10:51–62 (1986).

Mackinney, G., J. Biol. Chem. 140:315–322 (1941).

Beevers, L., Plant Biochemistry, J.Bonner and J. E.Varner (Eds), Academic Press, N.Y. pp. 771–794 (1976).

Bjorkman, O., and B. Dammig, Planta 170: 489–504 (1987).

Grover,et al., InPhotosynthesis:photoreactions to plant productivity, eds.Y.P.Abrol,P.Mohanty, GovindJee, 226–255 (1992).

Kura–Hotta et al., Plant and Cell Physiol 28(7) 1321–1329 (1987).

Sultemeyer,K.D., et al., Planta 189:235–242 (1993).

Mir, N.A., et al., Plant Physiol. 109:1295–1300 (1995).

NON-DESTRUCTIVE METHOD AND APPARATUS FOR DETECTION OF FRUIT AND VEGETABLE QUALITY

BACKGROUND OF THE INVENTION

(1) Summary of the Invention

The present invention relates to a non-destructive method and apparatus for detection of fruit and vegetable quality by use of fluorescence detection. In particular, the present invention relates to a method which uses a high intensity red light source for irradiation of the fruit or vegetable and a fluorescence detector to detect induced fluorescence from the red light at a frequency greater than that of the red light. The method is amenable to high speed automated conveyor systems and is reliable for detecting quality in the form of firmness, texture, color and/or aroma.

(2) Description of Related Art

The high level of competition in the domestic and international marketplaces for stored apple fruit requires high quality packed fruit. Segregating high- and low-quality fruit is an important component of quality control of the final packout. While packinghouses are able to segregate individual fruit by color and size, they are at present unable to sort each fruit by quality attributes that relate to condition (e.g., flesh firmness, sugar content, ratio of sugars to titratable acidity, aroma and ability to retain these quality attributes).

During ripening and senescence, the quality of apple fruit with regard to color, texture and flavor changes dramatically. While some fruit such as 'Law Rome' or 'Rome Beauty', can become mealy (i.e., lose condition) without significant firmness loss firmness is still considered to be the most important overall quality attribute of the fruit selected by consumers (Dull, G. G., et al., Quality. In: A. C. Hulme (ed.) The biochemistry of fruit and their products. Vol. 2, 721–725 Academic Press, New York (1971)). Lovelidge, B., et al. (Grower 108:53–54 (1987)) reported that firmness correlated well with apple fruit crispness and juiciness, and suggested it is an indicator of overall fruit quality and texture. The primary disadvantage of the penetrometer (Magness-Taylor or MT) test is its destructive nature, which results in the use of small samples to estimate the firmness of a population. This feature limits use of firmness testing for on-line sorting in the produce industry.

Much effort has therefore been focused on relating firmness to various physical properties in a nondestructive fashion. Elastic modulus, which is a function of the resonant frequency of a material, has been assessed as measure of firmness (Abbott, J. A., et al, Food Technol. 22:101–112 (1968); Abbott, J. A., et al., J. Amer. Soc. Hort. Sci. 117:590–595 (1992); Armstrong, P. R., et al., Transactions of the ASAE 33:1353–1359 (1990)). Resonant frequencies have been found to decrease during storage, maturation and ripening (Liljedahl, L. A. and J. A. Abbott, Trans. ASAE (1994)). However, the relationship between firmness and the elastic modulus as determined by mechanical vibration, sonic transmission and acoustic impulse tests has not been good enough to warrant widespread use of this technology (Abbott, J. A., et al., J. Amer. Soc. Hort. Sci. 117:590–595 (1992)).

Chloroplast fluorescence is used by photobiologists to investigate photosynthetic reactions (Mishra, P. K. and G. S. Singhal, Plant Phys. 98:1–6 (1992); Van Kooten, O., et al., Photosyn. Res. 25:147–150 (1990)) and has, more recently, been widely used by plant physiologists and breeders to reveal physiological stress and to identify stress-resistant selections (Schreiber, U., and W. Bilger, Progress in Botany 54:151–173 (1993)). Collectively, studies on chlorophyll fluorescence indicate that it is a helpful tool for investigating physiological activities of plants.

Chlorophyll fluorescence has been used as a measure of whole plant and plant organ plant physiological status. Fluorescence is induced by direct excitation of chlorophyll molecules of photosystem II (PSII) by light and their immediate relaxation. When PSII is functioning poorly, fluorescence characteristics are altered. Stresses such as chilling injury (van Kooten, O., and Snell, Photosyn. Res. 25:147–150 (1990)) and high temperature stress (Havaux, M., et al., Planta 186:88–89 (1991)) can be detected as a reduction in PSII function. For banana and mango, chlorophyll fluorescence declines with ripening, probably due to chlorophyll loss and a loss in chloroplast competence (Smillie, R. M., et al., Applications of chlorophyll fluorescence to the postharvest physiology and storage of mango and banana fruit and the chilling tolerance of mango cultivars. Asean Fd. J. 3:55–59 (1987)). Chlorophyll fluorescence has also been proposed as an indicator of physiological disorders in stored apples related to low $O_2$ and high $CO_2$ damage (DeEll, J. R., et al., HortScience 30:782 (1995)). Beaudry, R., et al., HortScience 30:816 (1995) found a decline in fluorescence parameters for apple fruit during regular air (RA) storage and suggested a relationship exists between the decline in chloroplast competency and the development of apple scald.

There is general agreement that membrane deterioration is a fundamental aspect of senescence that is initiated early in the senescence process (Meir, S., et al., Postharvest Biol. Tech. 2:125–135 (1992); Thompson, J. E., The molecular basis for membrane deterioration during senescence. In: L. D. Nooden and A. C. Leopold (eds.). Senescence and aging in plants. Academic Press, NY. P. 51–83 (1988)). While the membrane of chloroplasts retain their physical integrity until late in senescence, photosynthetic capacity also declines from the earliest stages of senescence (Gepstein, S., Photosynthesis. In: L. D. Nooden and A. C. Leopold (eds) Senescence and aging in plants. Academic press, NY. P. 85–109 (1988)). Giersch and Krause (Giersch, C., et al., Photosyn. Res. 30:115–121 (1991) demonstrated a quasi-linear relationship between Fv/Fm and the photosynthetic capacity of PSII. Significantly, Hariyadi and Parkin (Hariyadi, P., et al., Postharvest Biol. Technol. 1:33–45 (1991)) demonstrated that destruction of PSII related to the peroxidative decay of cell membranes.

Most techniques for measuring apple condition are limited in usefulness by having a poor relationship to overall quality, being destructive in nature and/or requiring excessive analysis time. As a result, most packinghouses choose to simply monitor firmness and, to a lesser extent, sugar content or brix at the time of packing. Since the fruit used in these measurements are destroyed, the fruit for which measures of quality exist are discarded. Importantly, a relatively small number of fruit are taken to represent a population of fruit, which may number in the millions. If quality attribute values are normally distributed within a population, fruit-to-fruit variation would allow a large number of low-quality fruit in the population to be packed for fresh consumption. In an effort to reduce the delivery of unacceptable fruit to the consumer, a non-destructive technology for packingline sorting based on one or more of the attributes of condition is actively being sought. Nondestructive sensing technologies evaluated and/or employed for estimating the quality of apple fruit include: light reflection, light transmission, delayed light emission, fluorescence, light spectroscopy, X-ray, magnetic resonance, image processing, force-deflection response, impact response, mechanical vibration response, acoustic response, dielectric response, microwave response, density specific gravity and gas analysis (Brown, G. K., and Y. Sarig, ASAE 05-94. Nondestr. Technologies for Quality Evaluation of Fruits and Vegetables, p. 120–147, Amer. Soc. Ag. Engin., St. Joseph Mo. (1994)).

Assessment of the physiological status of the living green tissues with chloroplast fluorescence is known. The chloroplast fluorescence results from the reactions of deexcitation of excited chlorophyll molecules. Under ideal conditions, most of the energy from excited molecules is trapped into chemical energy which reduces the fluorescence yield often designated as chlorophyll fluorescence quenching. The amount and degree of variable fluorescence is a measure of chloroplast activity (Mir, N. A., et al., Plant Physiol 108:313–318 (1995)). The inventors have found that chloroplast fluorescence declined as the apple fruit aged in air-storage and suggested chlorophyll fluorescence as a non-destructive tool for quality measurement of stored apple (Beaudry, et al., Hort Science 30:816 (1995)). Chlorophyll fluorescence has also been reported as a powerful tool for detecting low-$O_2$ or high-$CO_2$ stress in long-term stored apple (DeEll, J. R., et al., HortScience 30:782 (1995)). For banana and mango, chlorophyll fluorescence declined with ripening, probably due to chlorophyll degradation and a loss in chloroplast competence (Smillie, R. M., et al., Asean Fd. J. 3:55–59 (1987)).

U.S. Pat. Nos. 2,933,613 to Powers, 3,773,172 to McClure et al., 3,930,994 to Conway et al., 3,980,181 to Hoover et al., 3,998,555 to Hanscom et al., 4,106,628 to Warkentin et al., 4,132,314 to von Beckmann et al., 4,170,306 to Marshall et al., 4,205,752 to Malvick et al., 4,281,933 to Houston et al., 4,330,062 to Conway et al., 4,476,982 to Paddock et al., 4,558,786 to Lane, and 5,401,954 to Richert, and Japanese 63-246639 describe various types of color detecting apparatus for determining the quality of a fruit or vegetable. Such measurements are not based upon determinations of a fluorescent response of the fruit or vegetable to be tested and are generally not sufficiently reliable for commercial processing.

OBJECTS

It is therefore an object of the present invention to provide a nondestructive method and apparatus for estimating quality of a harvested fruit, particularly firmness, texture, color and aroma. Further, it is an object of the present invention to provide an apparatus which is relatively inexpensive to construct and which has a high degree of reproducibility of result. These and other objects will become increasingly apparent by reference to the following description and the drawings.

Traces along X-axis represents frequency distributions of firmness of CA (solid line) and RA (dashed line) fruit. The percent RA fruit incorrectly identified as "CA-stored" (dashed line, FIG. 9B) and CA fruit incorrectly identified as "RA-stored" (solid line, FIG. 9B) are depicted. Accuracy reflects percent RA and CA fruit that were correctly segregated.

Figure 10:
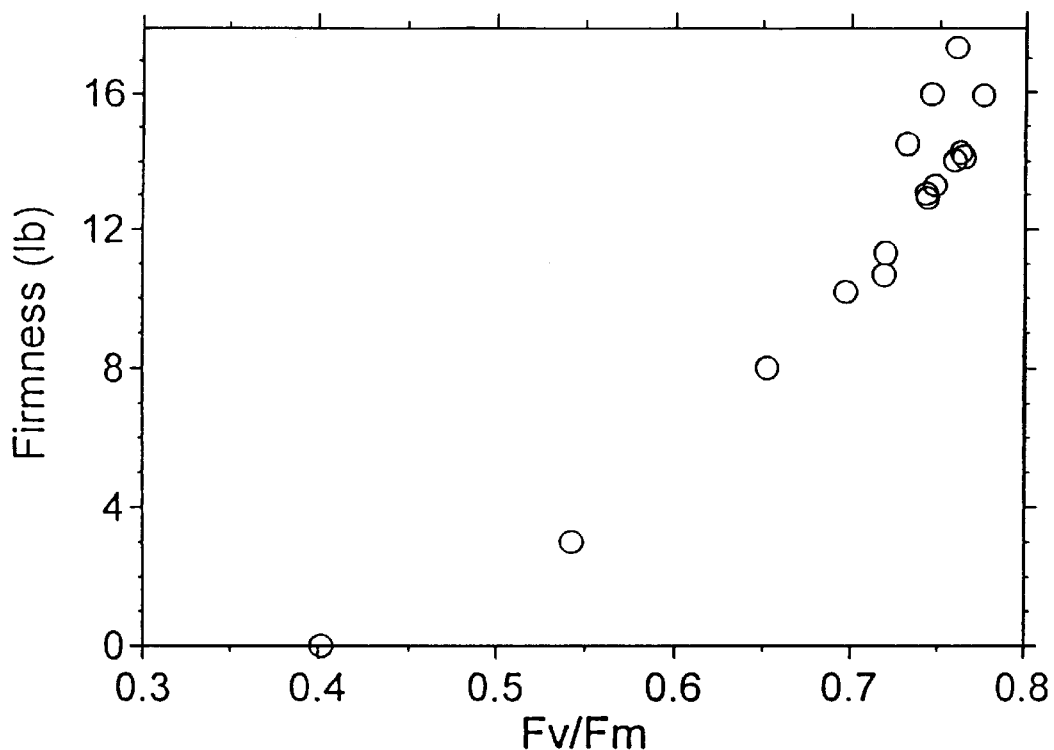

FIG. 10 is a graph showing relationship between firmness and fluorescence (Fv/Fm) for peach fruit at harvest.

Figure 11:
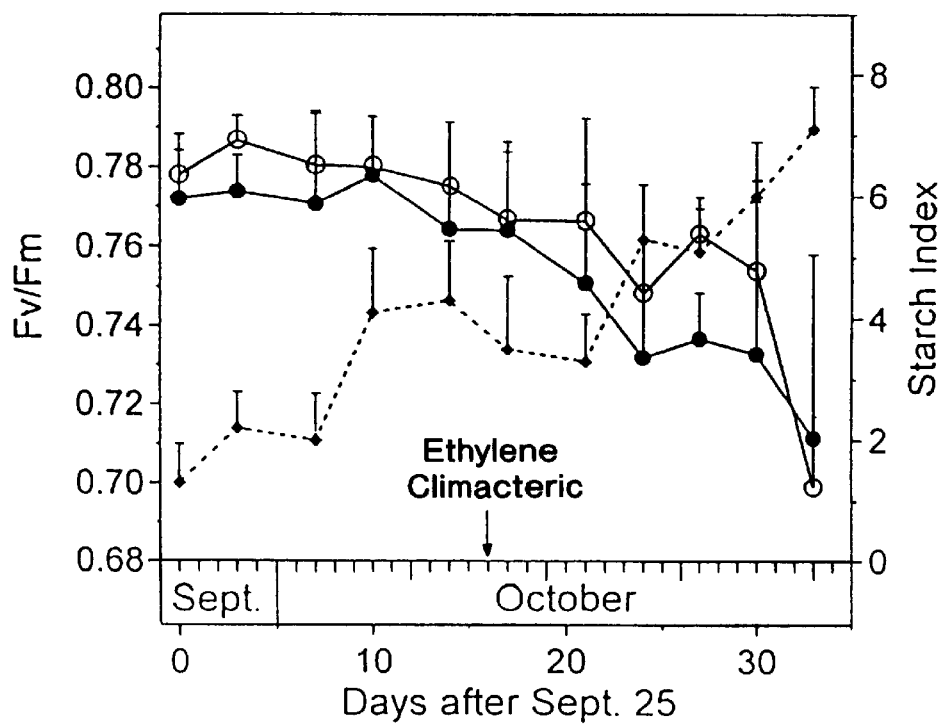

FIG. 11 is a graph showing effect of harvest date on fluorescence (Fv/Fm) of fruit held 3 (open circles) and 6 (solid circles) days at 23° C. in air. Diamonds represent scald index (1=immature, 9=overmature). Each data point represents 10 fruit. Bars represent 1 S.D.

Figure 12A:
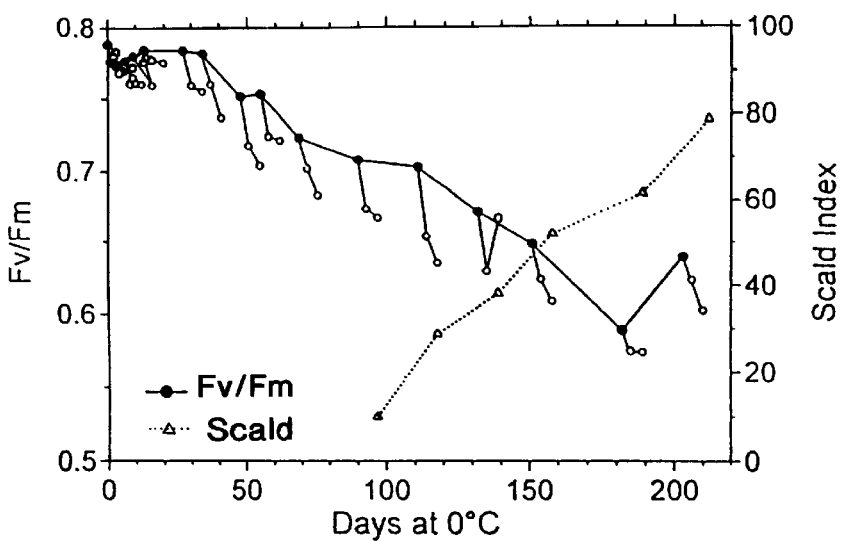
Figure 12B:
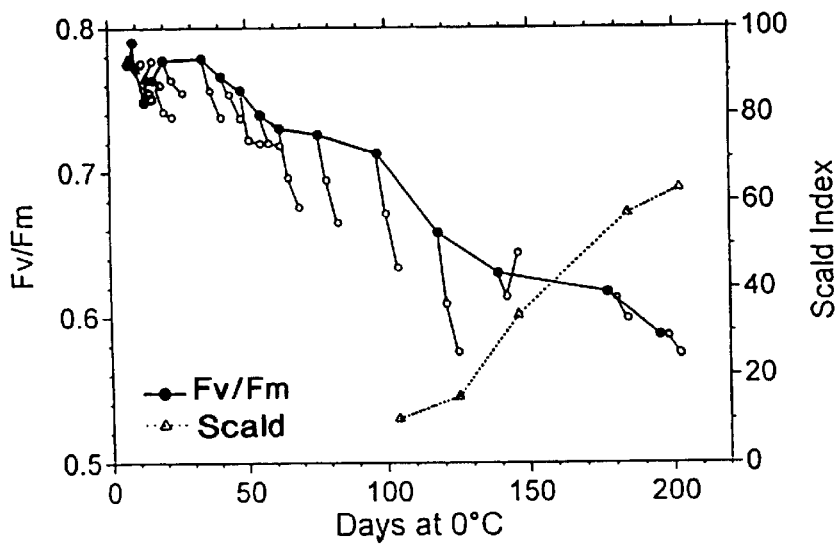
Figure 12C:
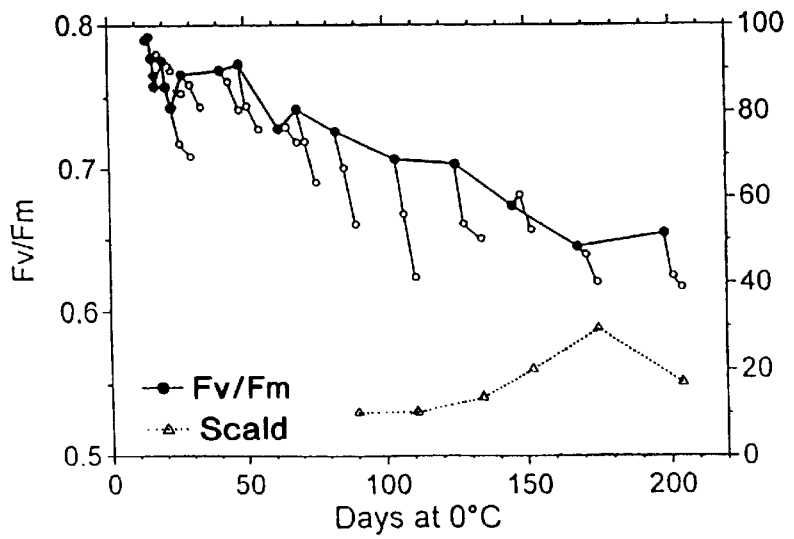

FIGS. 12A, 12B and 12C are graphs showing the effect of harvest date and storage duration on fluorescence (Fv/Fm) and scald incidence of 'Red Delicious' apple fruit stored at 0° C. in air. Fruit were harvested Sept. 1, (A); Oct. 3 (B, commercial harvest date); and Oct. 10, (C). Fluorescence was assessed upon removal from storage (solid circles) and after 3 and 7 days at 23° C. in air (open circles).

Figure 13:
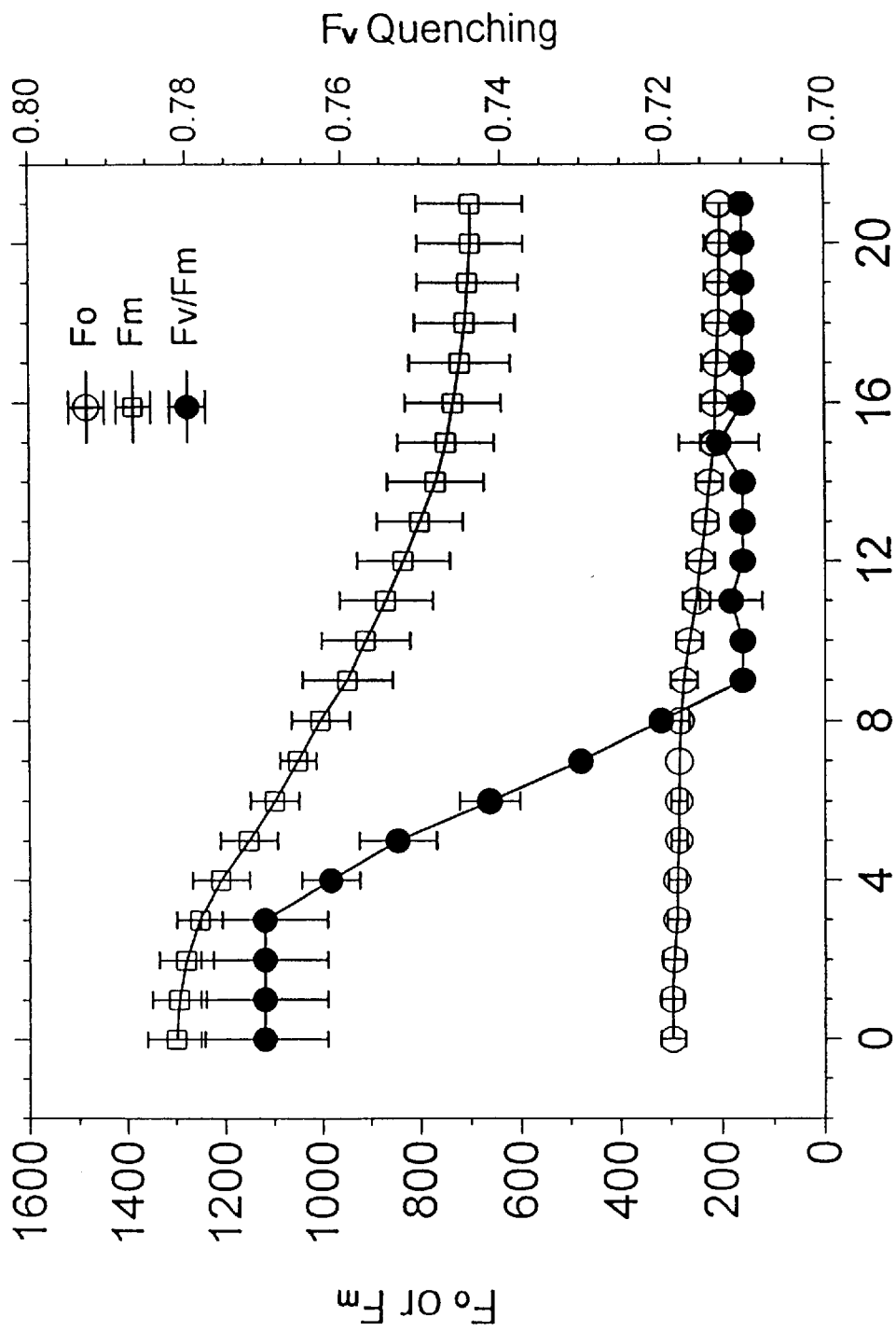

FIG. 13 is a graph showing decline in chloroplast fluorescence parameters for 'Golden Delicious' apple fruit following removal from refrigerated air-storage for 2 months. Fruit were held in air at 23° C. for 22 days. Each data point is an average of seven fruit. a: $F_o$; b: $F_m$; c: $F_v/F_m$.

Figure 14:
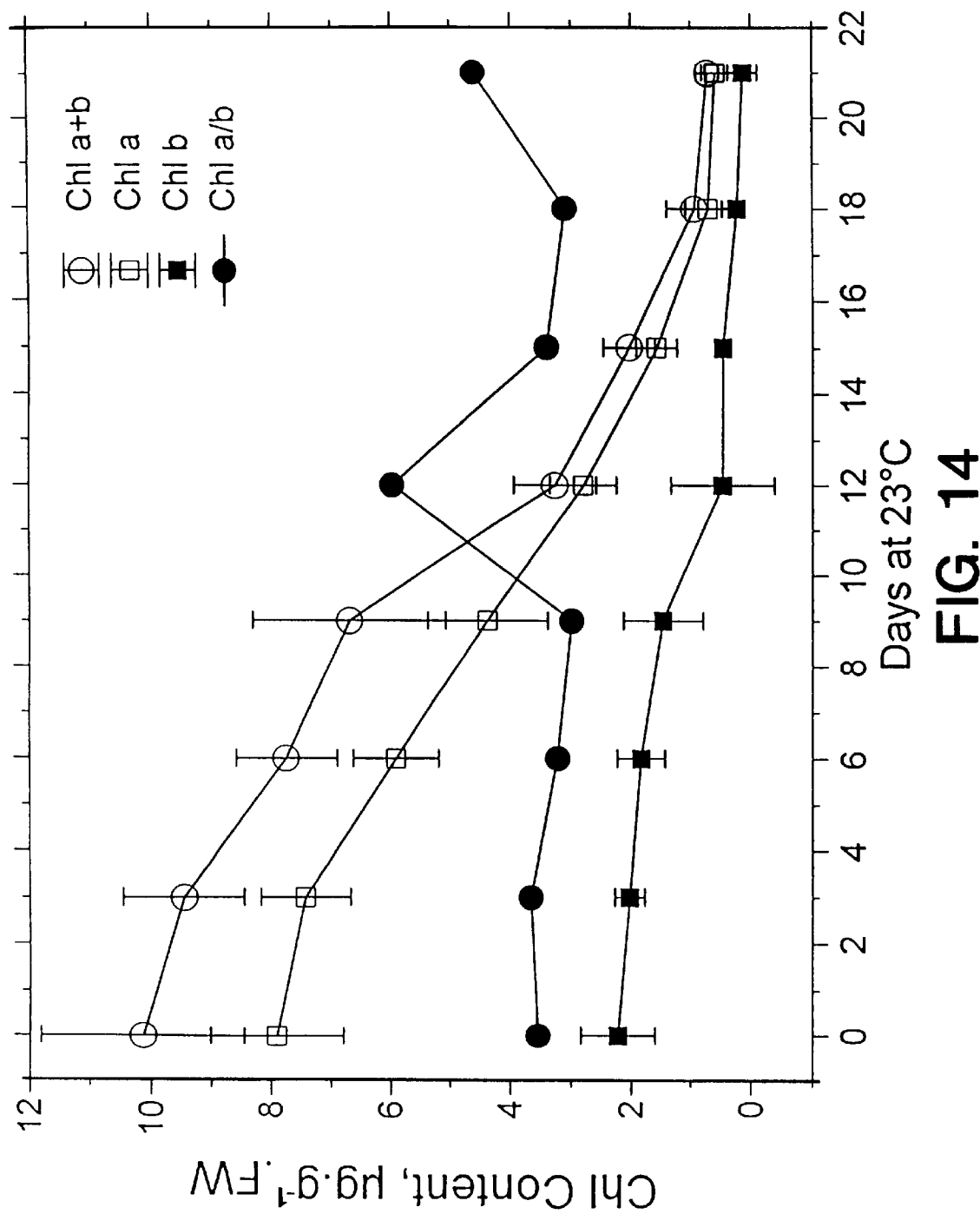

FIG. 14 is a graph showing decline in chlorophyll concentration for 'Golden Delicious' apple fruit following removal from refrigerated air-storage for 2 months. Fruit were held in air at 23° C. for 22 days. Each data point is an average of 5 samples.

Figure 15:
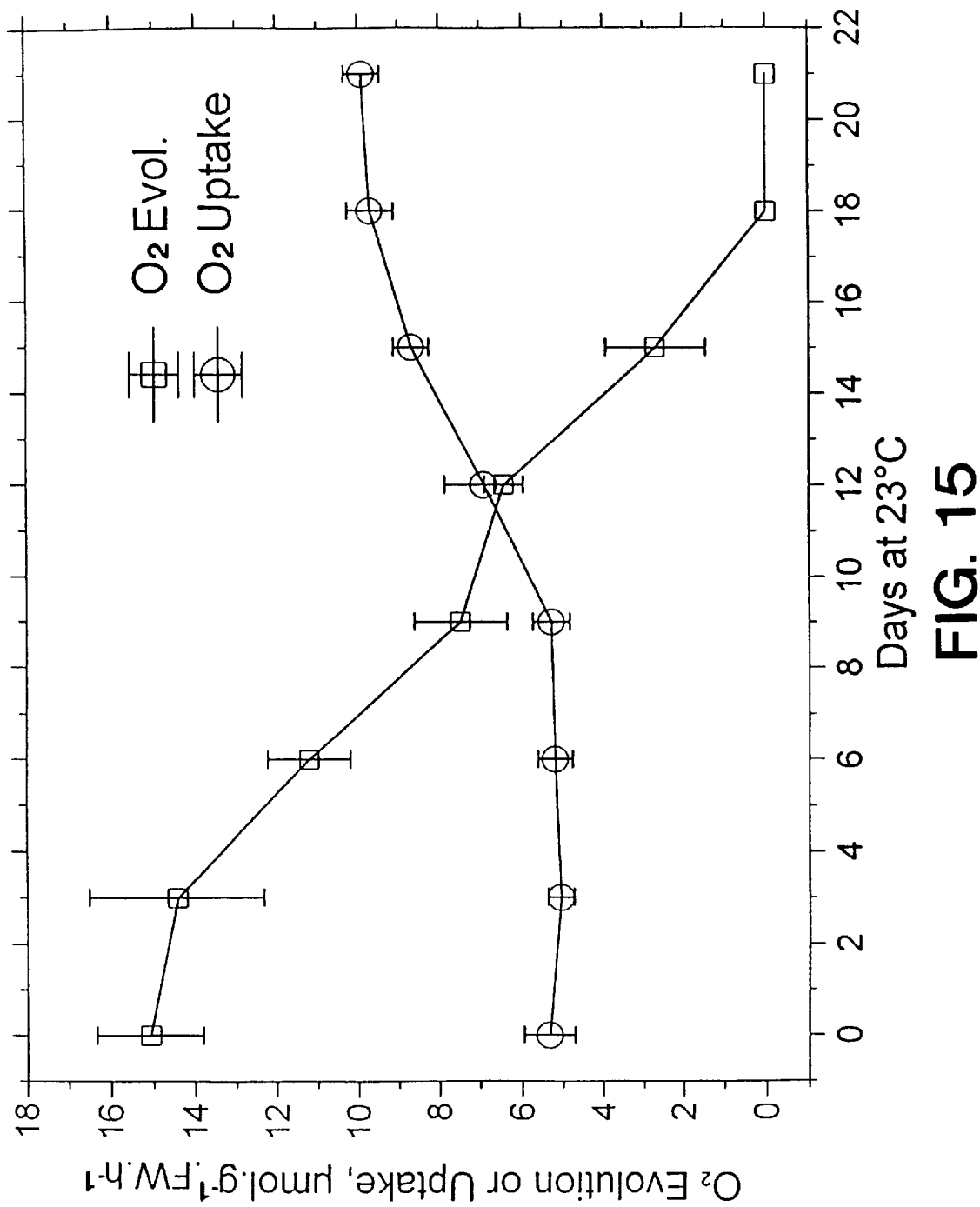

FIG. 15 is a graph showing decline in chloroplast activity for 'Golden Delicious' apple fruit following removal from refrigerated air-storage for 2 months. Fruit were held in air at 23° C. for 22 days. Each data point represents three to five fruit.

Figure 16:
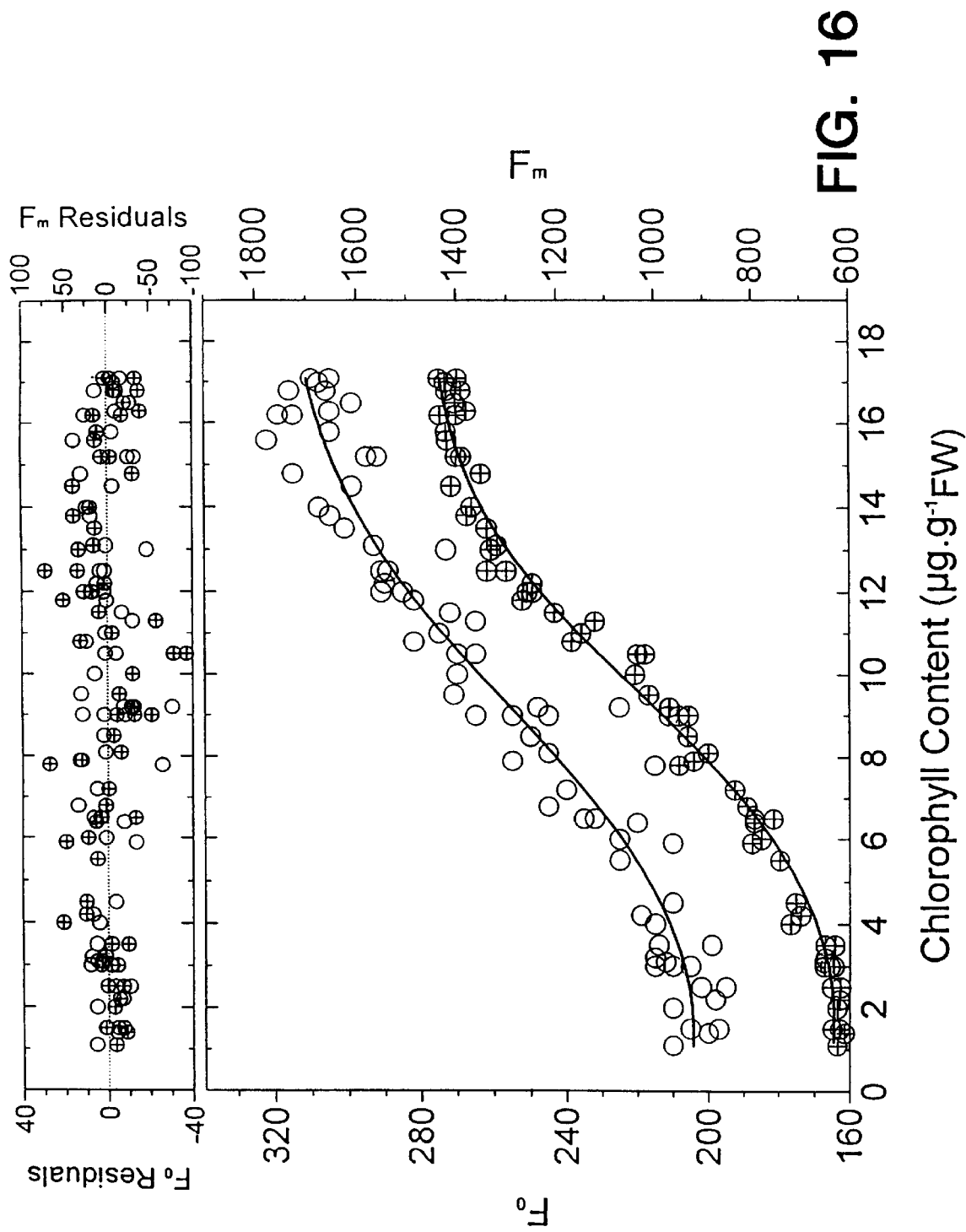

FIG. 16 is a graph showing the relationship between fluorescence parameters, $F_o$ and $F_m$ and Chlorophyll concentration for 'Golden Delicious' apple fruit following removal from refrigerated air-storage for 2 months. Fruit were held in air at 23° C. for 22 days. Line represents best fit curvilinear equations.

Figure 17:
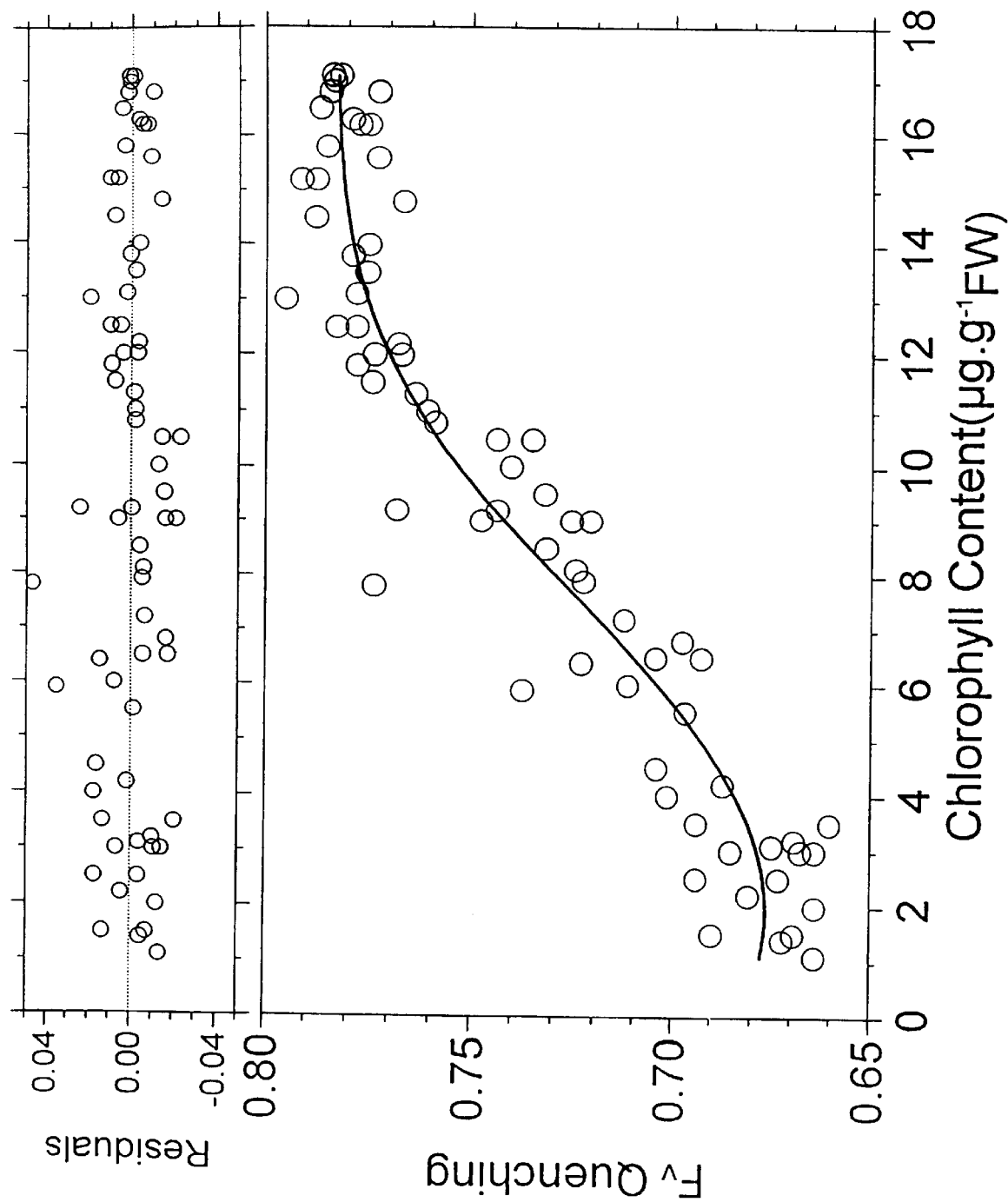

FIG. 17 is a graph showing the relationship between fluorescence ($F_v/F_m$) and Chlorophyll concentration for 'Golden Delicious' apple fruit following removal from refrigerated air-storage for 2 months. Line represents best fit curvilinear equations.

Figure 18:
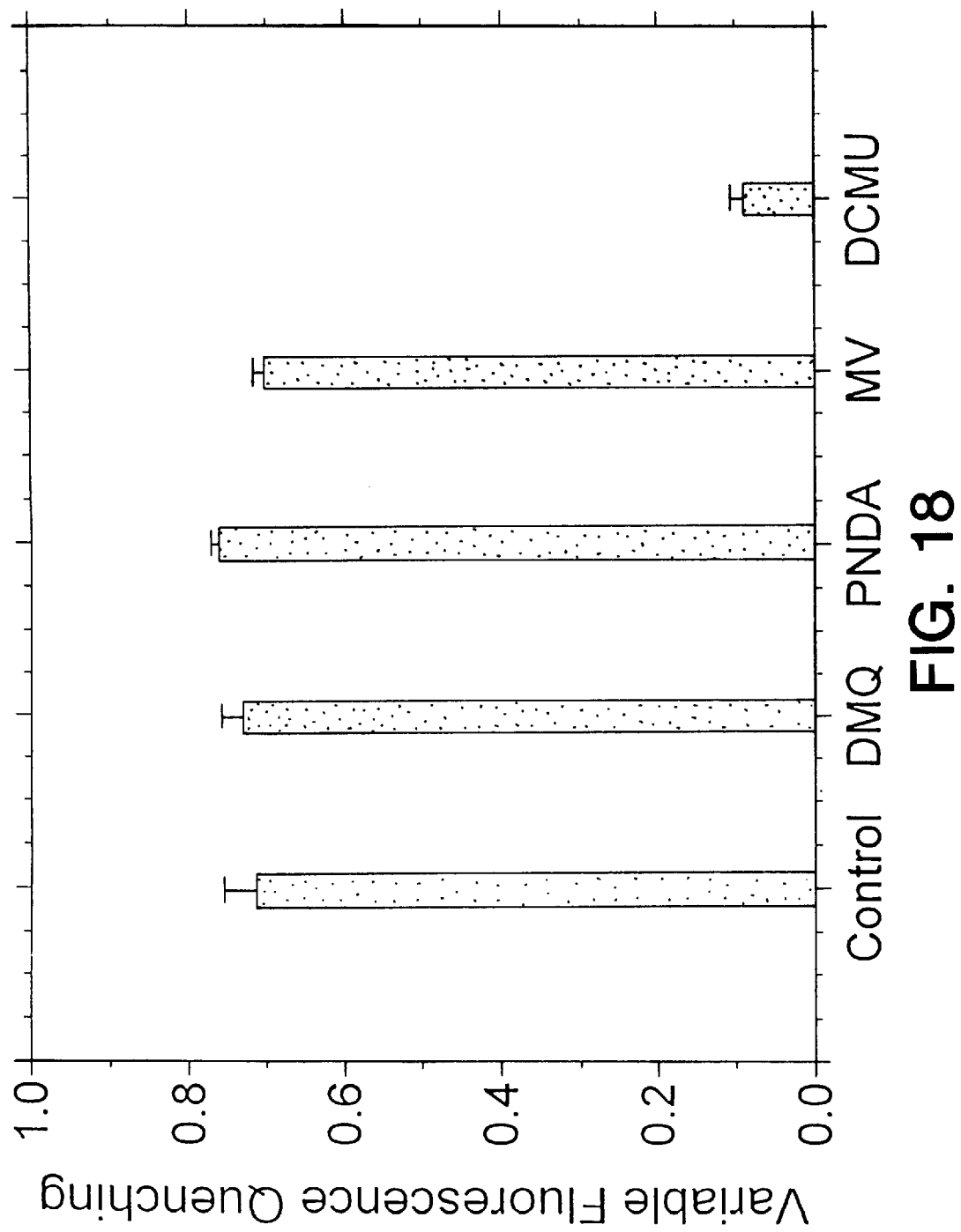

FIG. 18 is a graph showing the influence of artificial electron acceptors and inhibitors of photosynthetic electron transport chain in apple. The data are average of 9 to 15 values.

Figure 19:
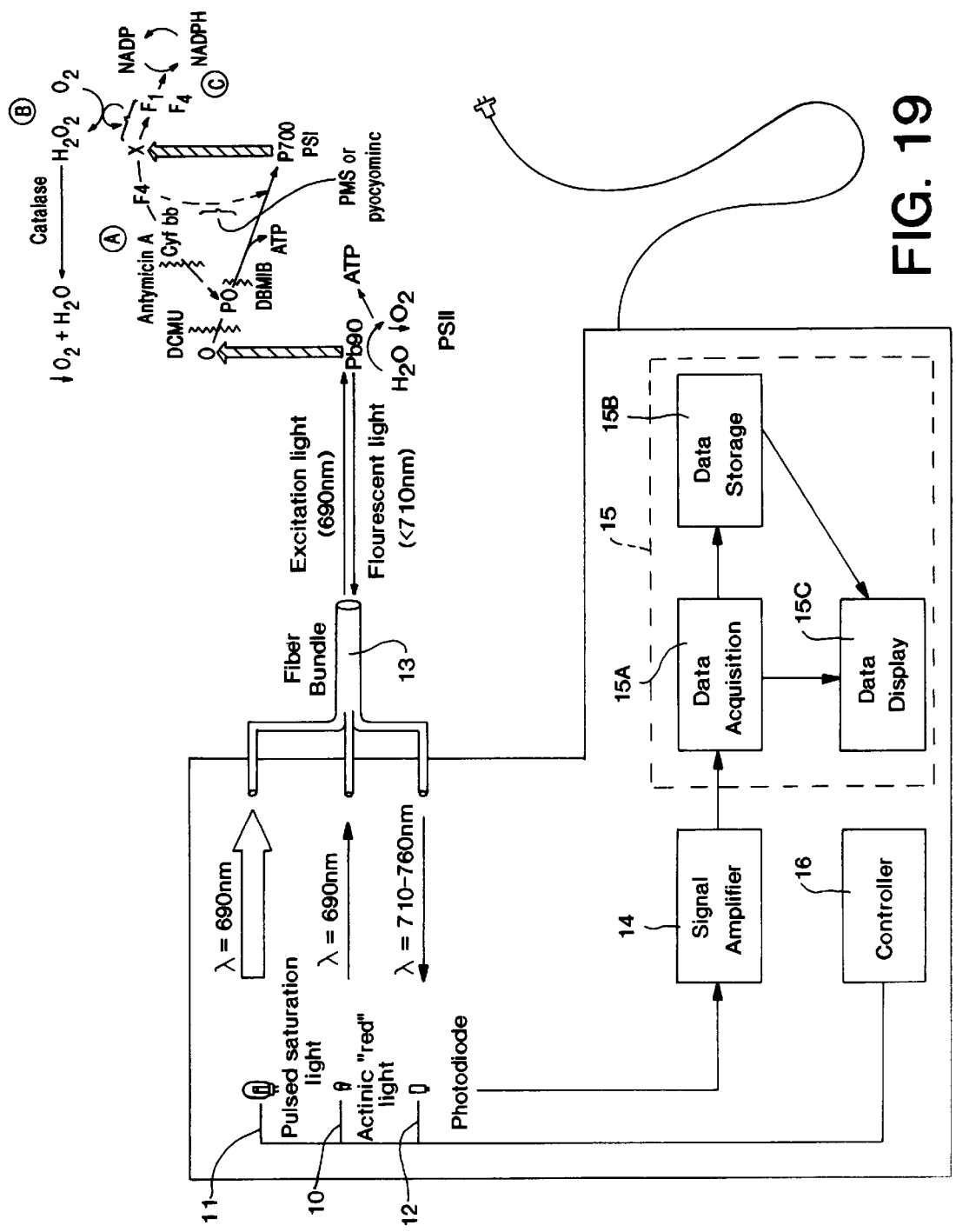

FIG. 19 is a schematic view of a fruit and vegetable quality detector. Light (690 nm) is emitted from actinic light source 10 and fluorescent light from photosystem II (P 690—comprised of chlorophyll within the plant material) is detected by the photodiode 12 to generate Fo. After a brief time (approx. 0.2 sec.) the saturation source 11 is illuminated, overwhelming photosystem II; resulting fluorescence is taken as Fm (maximal fluorescence). The detected signals are amplified, digitized and stored and displayed. The controller initiates and controls illumination sequences and brightness.

DESCRIPTION OF PREFERRED EMBODIMENTS

The present invention relates to a method for indirectly estimating quality of a harvested, edible fruit or vegetable having a skin which comprises:
  (a) exposing the skin of the fruit or vegetable to a source of red light which induces a fluorescence intensity at a frequency above the red light from chlorophyll in the skin of the fruit or vegetable;
  (b) detecting the fluorescence intensity produced by the skin; and
  (c) estimating the quality of the fruit or vegetable as a function of the intensity of the fluorescence detected, wherein when the fruit or vegetable has a first level of the fluorescence of the chlorophyll in the skin when the fluorescence intensity is relatively high which is indicative of an acceptable quality and wherein the intensity of the fluorescence of the chlorophyll at a second level which is decreased and which is indicative of an unacceptable quality.

Further the present invention relates to a method for indirectly estimating quality of a fruit or vegetable having a skin which comprises:
  (a) exposing the skin of the fruit or vegetable to an applied continuous first source of light including red light which induces a background fluorescence intensity ($F_o$) and to a second source of light which provides a maximal fluorescence intensity ($F_m$) from the skin of the fruit or vegetable at a longer wavelength than the active light;
  (b) detecting the fluorescence intensities $F_o$ and $F_m$ produced by the skin;
  (c) determining a fluorescence intensity ratio of $$\frac{F_m - F_o}{F_m}$$

wherein $F_m - F_o$ is equal to a variable fluorescence intensity $F_v$; and
  (d) estimating the firmness of the fruit or vegetable as a function of the ratio, wherein the fruit or vegetable which has a first level of the chlorophyll in the skin as determined by the fluorescence intensity ratio has an acceptable quality and wherein the florescence intensity ratio is at a second level which is decreased and which is indicative of an unacceptable quality.

The present invention also relates to an apparatus for indirectly estimating quality of a harvested, edible fruit or vegetable which comprises:
  (a) light source means for exposing the fruit or vegetable to a red light which induces a fluorescence intensity at a wavelength greater than that of the red light from the skin of the fruit or vegetable;
  (b) detection means for detecting the fluorescence intensity from the fruit or vegetable; and
  (c) calculator means for converting the intensity of the fluorescence into a measure of the quality of the fruit or vegetable, wherein the fruit or vegetable which has a first level of the chlorophyll in the skin as determined by the fluorescence intensity which is indicative of an acceptable quality and wherein the fluorescence intensity is at a second level which is decreased and which is indicative of an unacceptable quality.

The present invention also relates to an apparatus for estimating quality of fruit or vegetable having a skin which comprises:
  (a) a first light source of red light which is modulated and is a monochromatic;
  (b) a second light source which is continuous and produces an actinic light including red light;
  (c) fiber optic means comprising individual fibers in a bundle with one end in a spaced apart relationship with a fruit or vegetable, wherein a first of the group of the fibers are illuminated by the second light source to provide the actinic light at the one end, a second of the group of the fibers which are periodically illuminated by the first light source to provide the pulsed light at the one end and a third of the group of the fibers which directs fluorescent light from the fruit or vegetable produced by each of the first or second light sources at the one end; and
  (d) detection means connected to the third group of the fibers with circuit means for determining a first fluorescence intensity ($F_o$) produced by the second light source and for determining a fluorescence intensity ($F_m$) produced by the high intensity light source for calculating a fluorescence intensity ratio of $$\frac{F_m - F_o}{F_m}$$

which when $F_m - F_o$ is equal to a variable fluorescence intensity ($F_v$), wherein the fruit or vegetable has chlorophyll in the skin as determined by the fluorescence intensity ratio which is at a first level indicative of an acceptable quality and wherein the fluorescence intensity ratio is at a second level which is decreased and which is indicative of an unacceptable quality.

A fruit or vegetable is a natural product of a plant which is used for some purpose, usually for animal or human consumption. These natural products have skins or leaves which contain chlorophyll, which converts sunlight into energy in the plant.

The term "red light" means light with wavelengths in the range of 650 to 690 nanometers (NM).

The fluorescence intensity of the chlorophyll generated by the red light is preferably between about 710–740 nm.

The equipment used to evaluate and detect the fruit or vegetable is shown in FIG. 19. An actinic red light source 10 is preferably used at a low intensity to irradiate the fruit or vegetable with red light (preferably near 690 nm). This provides a background fluorescence (Fo). A pulsed saturation red light source 11 is then used to irradiate the fruit or vegetable with a red light (preferably near 690 nm) to produce a maximal fluorescence intensity (Fm). The fluorescence intensity radiated from the fruit or vegetable is then detected by a photodiode 12. A fiber bundle 13 is preferably used to transmit the light from the sources 10 and 11 to the fruit or vegetable and then the fluorescence intensity is detected by the photodiode 12. The apparatus includes a conventional signal amplifier 14 and computer 15 for converting the signal to usable data, including data acquisition module 15A, data storage module 15B and data display module 15C. A controller 16 is used to sequence the steps in the method. As shown in FIG. 19, the red light of the low intensity light source 10 and the high intensity light source each generate light in a different manner. The excitation light source for Fo can be modulated at a set frequency (e.g. 1–2 KHz) and the resultant modulation in signal detected. Signal not associated with the modulated frequency can then be subtracted to reduce noise. The light source for the light for generating Fo should be a light-emitting diode. The higher intensity light for generating Fm can be a halogen light source or similar light that is continuous in nature and rich in red wavelengths.

Fluorescence measurements are rapid (0.3 to 0.8 s) and can be made at some distance from the plant surface. Thus a conveyor system can be used.

The objective of the following Examples was to determine the relationship between chloroplast fluorescence and standard quality indices of MT test firmness and ground color during fruit senescence immediately after storage and during an accelerated aging period after storage.

EXAMPLE 1

Materials and Methods

Fruit. Three apple (*Malus domestica* Borkh.) fruit cultivars, 'Red Delicious', 'Law Rome', and 'Golden Delicious', were selected from the study. 'Red Delicious' and 'Law Rome' fruit were stored for 4.5 months in controlled-atmosphere (CA) storage (0° C., 1.5% $O_2$, <3% $CO_2$) at the Clarksville Horticultural Research Station of Michigan State University. Additional 'Law Rome' fruit were held in regular air (RA) storage at 0° C. for the same duration. 'Golden Delicious' fruit were obtained after 4.5 months storage in a commercial CA facility (0° C., 1.7% $O_2$, <3% $CO_2$). The 'Red Delicious' and 'Golden Delicious' fruit were divided into two lots for "continuous" and "discrete" measurements. Continuous measurements were performed daily on the same seven fruit throughout the holding period; discrete measurements were made on a different set of five fruit every second day throughout the holding period.

The purpose of the continuous measurements was to view changes in fluorescence measurements on the same fruit to reduce the effect of variation within a fruit population, thereby more clearly demonstrating changes in fluorescence with time. The purpose of the discrete measurements was to permit destructive firmness measurements to be made and to relate changes in firmness with changes in fluorescence. 'Golden Delicious' fruit were included in the study because their lack of red pigmentation permitted the measurement of background color changes.

Holding periods were eighteen days for 'Golden Delicious' fruit and nineteen days for 'Red Delicious' fruit. During the holding period, fruit were kept at 22° C. in opaque black plastic bags to avoid moisture loss and light effects. All measurements were taken at 22° C. 'Law Rome' fruit were used to determine whether fluorescence could be used as a tool to segregate high quality (CA-stored) fruit from low quality (RA-stored) fruit. After storage, fruit were randomly selected from several bins of RA- and CA-stored fruit. For the CA and RA treatments, 192 and 169 fruit were used, respectively. Individual fruit were coded and RA and CA fruit were mixed so the test operator would have no knowledge of fruit history. Fruit were warmed to 22° C. and fluorescence and firmness determined. Additionally, to investigate whether the degree of color interferes with measuring fluorescence, a subset of the CA-stored 'Law Rome' fruit were segregated into three color grades, ten fruit per grade, and fluorescence measurements taken.

Chlorophyll fluorescence. Fluorescence measurements were made in a darkened laboratory. Apple fruit were placed 4 mm from the end of the fiber optic light guide of a pulse-modulated fluorometer (Model OS-500, Opti-Science, U.S.A.). The fluorometer was run in the "Fv/Fm" mode of operation; fluorescence was measured using a photodiode in the wavelength range 710–760 nm. During a run, minimal fluorescence (Fo) was monitored for 0.2 sec at a rate of 100 readings per second (20 sample points). The excitation (modulated) light (660 nm, with a filter for >700 nm light) intensity for the Fo measurement was approximately 0.15 $\mu$mol·m$^{-2}$·s$^{-1}$ (OS-500 setting=60) which was sufficient to get an accurate measurement of Fo (Van Kooten, O., et al., Photosyn. Res. 25:147–150 (1990)). The addition of approximately 3 mW (OS-500 setting=50) of continuous far red light (735 nm) did not influence fluorescence, therefore we assumed that the redox components of the electron transport chain were fully oxidized. After Fo was determined, the sampling rate was then increased to 1000/s and a saturation light (660 nm) pulse was supplied via the light guide by a halogen lamp. The light intensity at the peel during the pulse was estimated to be 2,400 $\mu$mol·m$^{-2}$·s$^{-1}$ photosynthetically active radiation (PAR) based on an OS-500 setting of 60; a setting of 255 yields approximately 10,000 $\mu$mol·m$^{-2}$·s$^{-1}$ PAR. The pulse duration was 0.8 s and a cut-off filter, blocking light above 700 nm, was used to prevent saturation of the photodiode. During the pulse, the maximum level of modulated chlorophyll fluorescence was designated as Fm. Three readings per fruit were taken at equidistant positions around the equator of each fruit and averaged. The efficiency of photosystem II (Fv/Fm) was calculated as (Fm–Fo)/Fm (Van kooten, O., et al., Photosyn. Res. 25:147–150 (1990)).

Skin color. Skin color of 'Golden Delicious' apple fruit was measured with a Minolta Chromameter 300 (Minolta Camera Co., Ltd., Osaka, Japan) in the CIELAB (Comission Internationale de l'Eclairage, L* a* b*) mode. The instrument was calibrated using a white calibration plate (Y=94.9, x=0.3131, y=0.3200). Color readings were made at three positions on each fruit. Since the dominant color change in 'Golden Delicious' is a decrease of green (a less negative a*) and increase of yellow (more positive b*), the color measurements in this experiment were calculated as a*+b*, which was taken as a measure of "yellowness".

Firmness. The flesh firmness of fruit was measured manually using a drill-stand-mounted Effegi penetrometer fitted with an 11 mm diameter probe. The penetrometer was calibrated at 12 lb (53.4N) using a top-loading balance. Firmness was determined for the discrete measurement lots of 'Red Delicious' and 'Golden Delicious'. Two discs (approximately 2.5 cm dia.) of skin tissue were removed, one from the most highly colored side of the fruit and the second from the surface opposite the first. The penetrometer probe was pressed into the tissue to a depth of 8 to 9 mm in a single smooth motion requiring approximately 1 to 2 s. Data were recorded as lb and converted to N by multiplying by 4.45N/lb.

Results

Figure 1A:
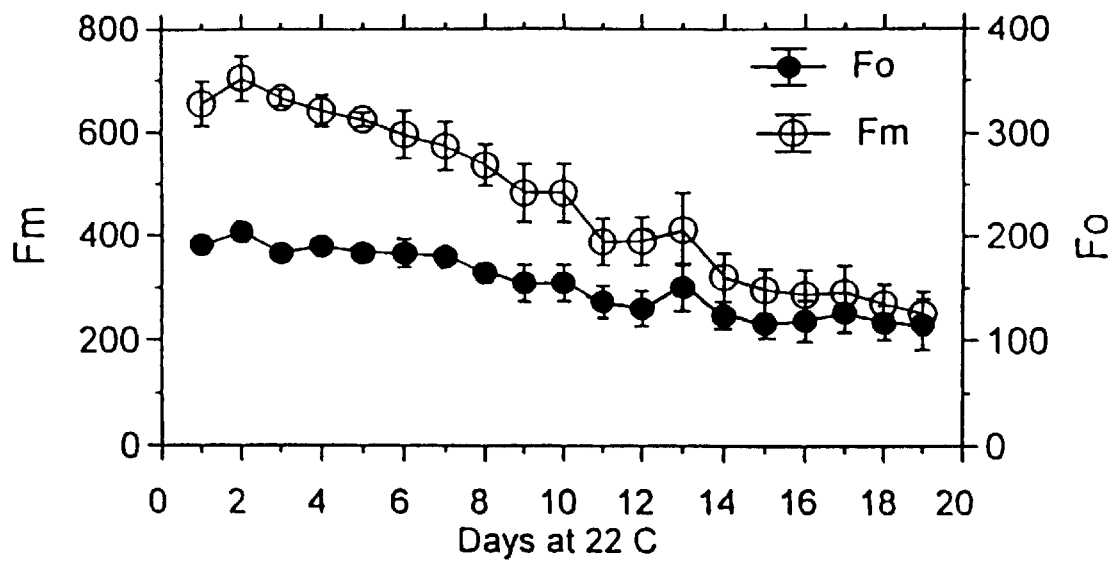
FIGS. 1A and 1B are graphs showing decline in chloroplast fluorescence parameters for seven continuously monitored 'Red Delicious' apple fruit at 22° C. in air following removal from controlled atmosphere (CA) storage (4.5 months at 1.5% $O_2$, <2.0% $CO_2$)
Figure 1B:
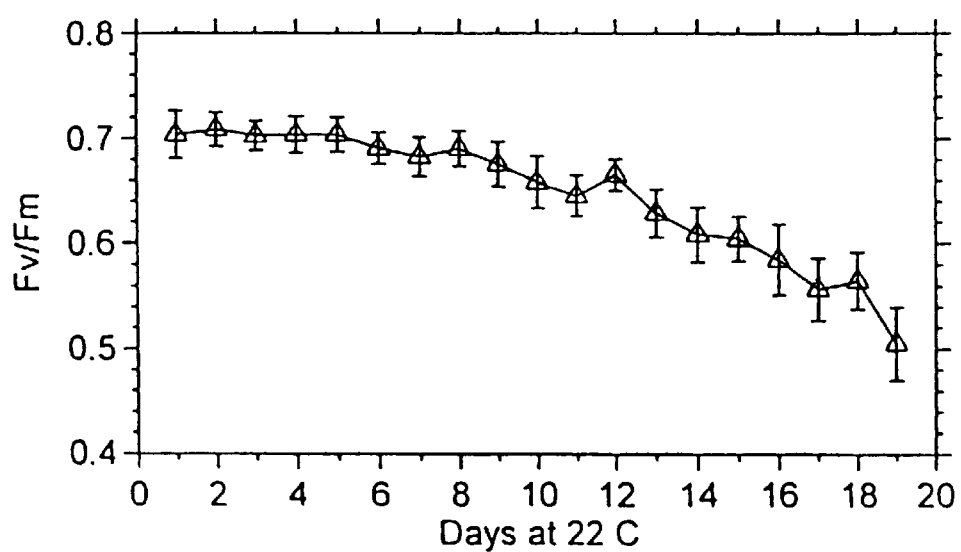
Figure 2A:
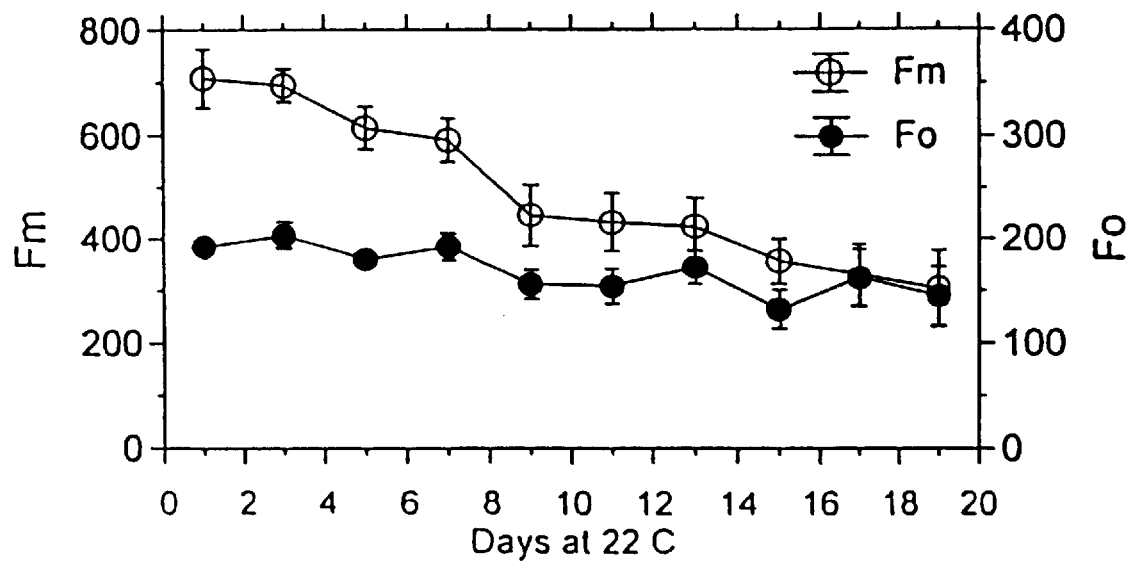
FIGS. 2A and 2B are graphs showing decline in chloroplast fluorescence parameters for discrete samples of 'Red Delicious' apple fruit at 22° C. in air following removal from CA storage (4.5 months at 1.5% $O_2$, <2.0% $CO_2$). Each data point represents five fruit.
Figure 2B:
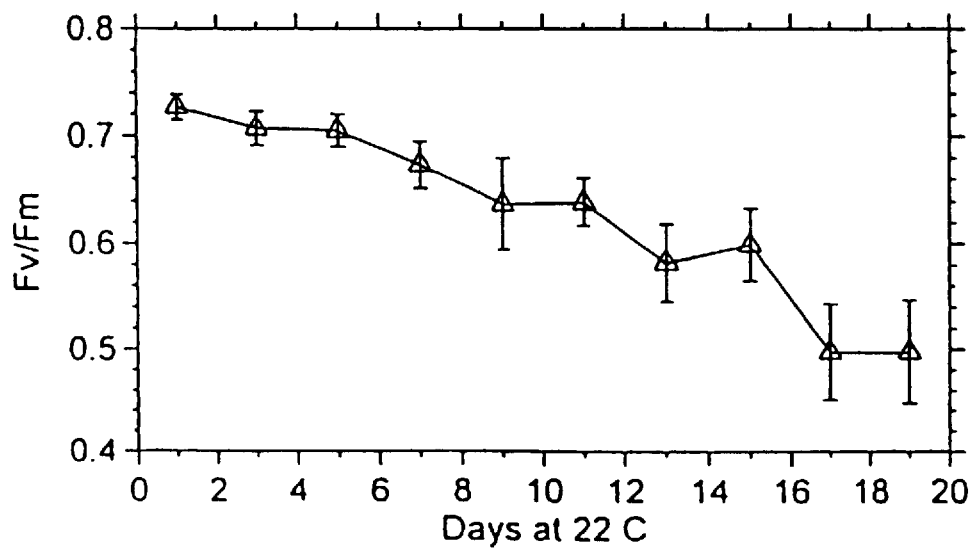
Figure 3:
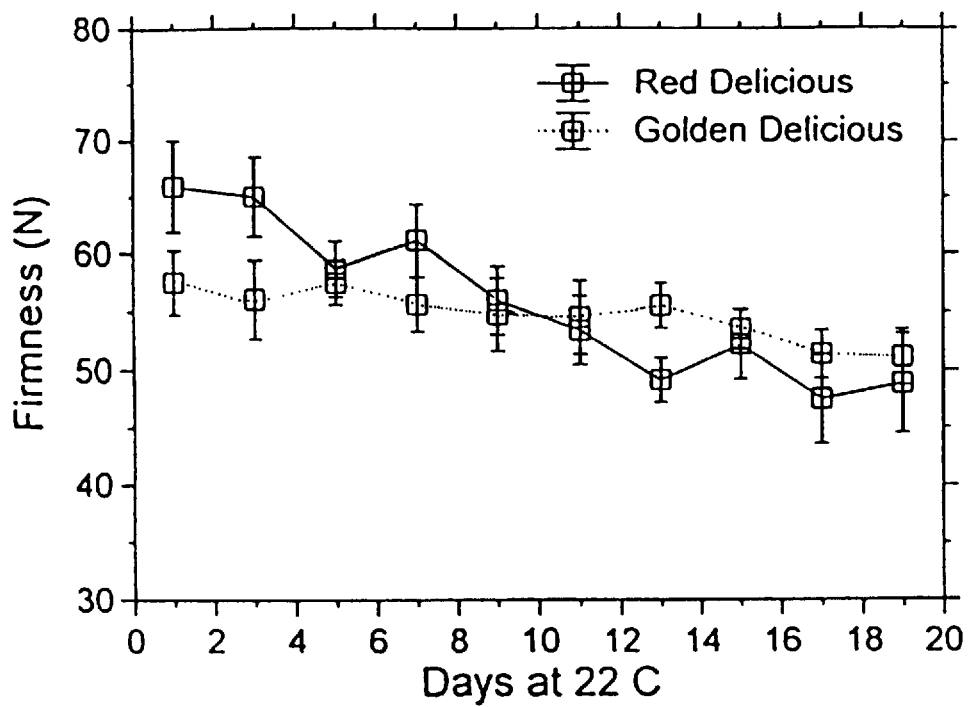
FIG. 3 is a graph showing change in firmness of discrete samples of 'Red Delicious' and 'Golden Delicious' apple fruit at 22° C. in air following removal from CA storage (4.5 months, 1.5% $O_2$, <2.0% $CO_2$). Each data point represents seven fruit.
Figure 4A:
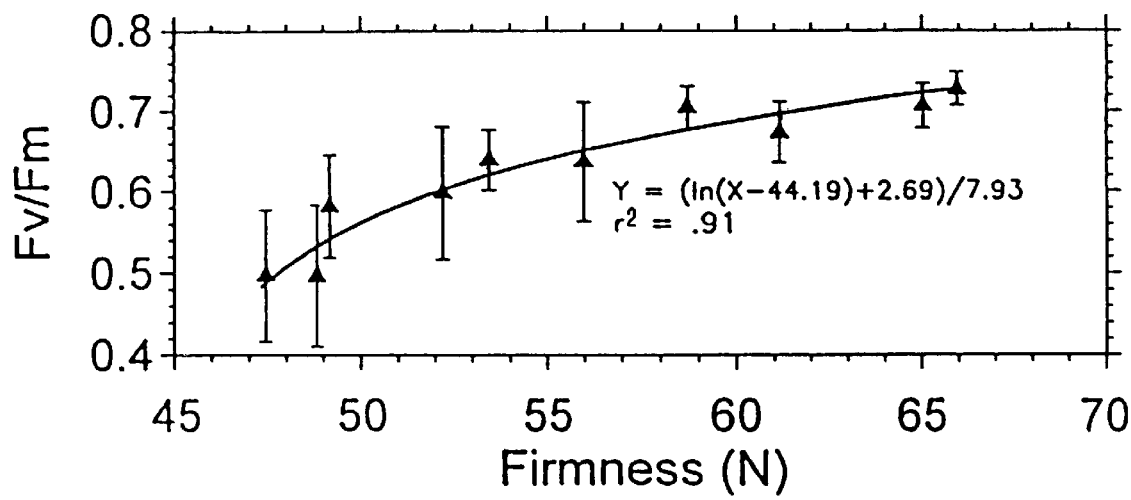
FIGS. 4A and 4B are graphs showing the relationship between fluorescence parameters and MT-firmness for 'Red Delicious' apple fruit following removal from CA storage (1.5% $O_2$, <2.0% $CO_2$) for 4.5 months. Each data point represents seven fruit. Lines represents best first curvilinear equations. The equation bars represent Mean ±S.E.
Figure 4B:
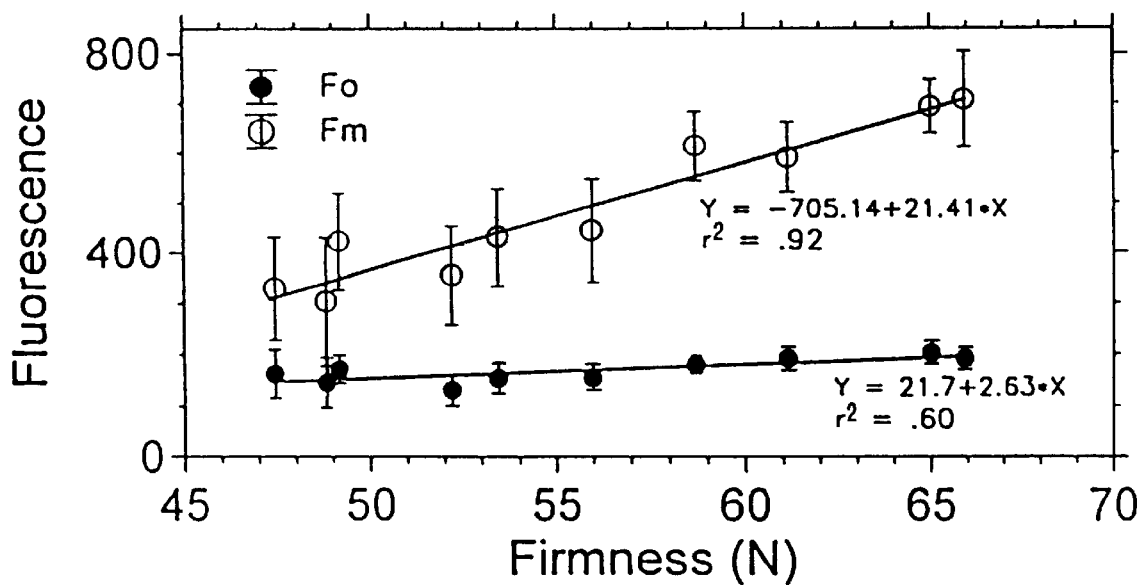

Post-storage changes in 'Red Delicious'. Fo, Fm and Fv/Fm declined with time for fruit for which continuous measurements were taken (FIGS. 1A and 1B). The decline began approximately 2–4 days after moving the fruit to room temperature (22° C.). Fo declined from 180 to 120 and Fm declined from 650 to 250. Fv/Fm declined from 0.7 to 0.5 over the 19-day holding period. However, unlike Fo and Fm, a decease relative to initial readings was not apparent until 9–10 days after transfer to 22° C. For fruit in the discrete measurement lot, the rates of decline in Fo, Fm, and Fv/Fm were similar to those in the continuous lot (FIGS. 2A and 2B). The firmness of 'Red Delicious' fruit decreased from approximately 66N at the beginning of the experiment to 49N (FIG. 3). When firmness was regressed against Fv/Fm, the data were highly correlated ($r^2$=0.91) and the relationship appeared to be non-linear (FIG. 4A). The decline in Fm was also correlated with firmness loss, but the relationship was linear ($r^2$=0.92). Fo was also linearly correlated ($r^2$=0.6) with firmness (FIG. 4B).

Figure 5A:
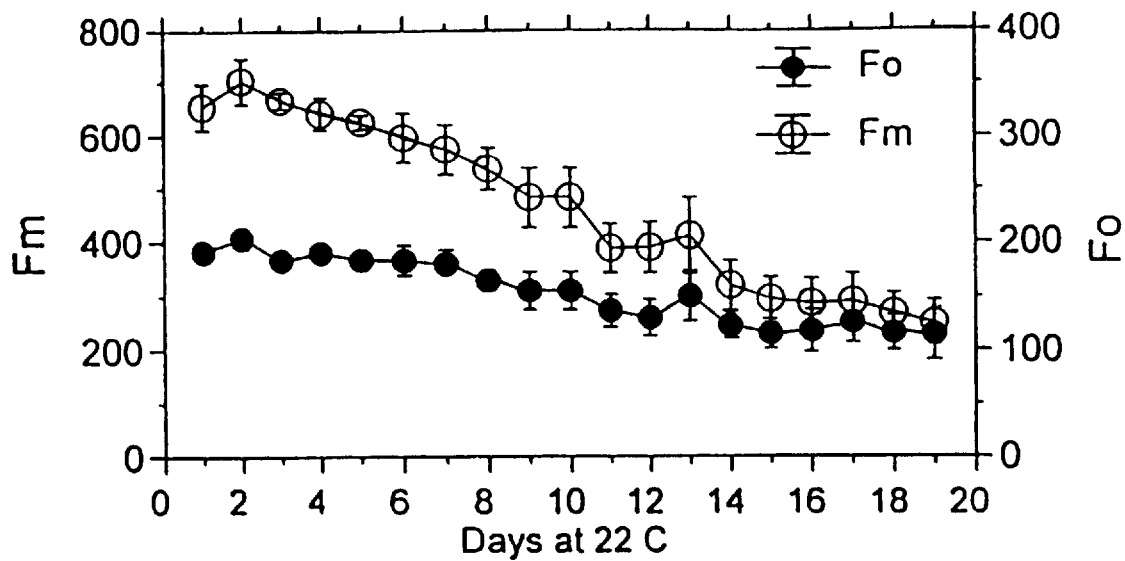
FIGS. 5A and 5B are graphs showing decline in chloroplast fluorescence parameters for seven continuous monitored 'Golden Delicious' apple fruit at 22° C. in air following removal from CA storage (4.5 months, 1.5% $O_2$, <2.0% $CO_2$). Bars represents ±S.E.
Figure 5B:
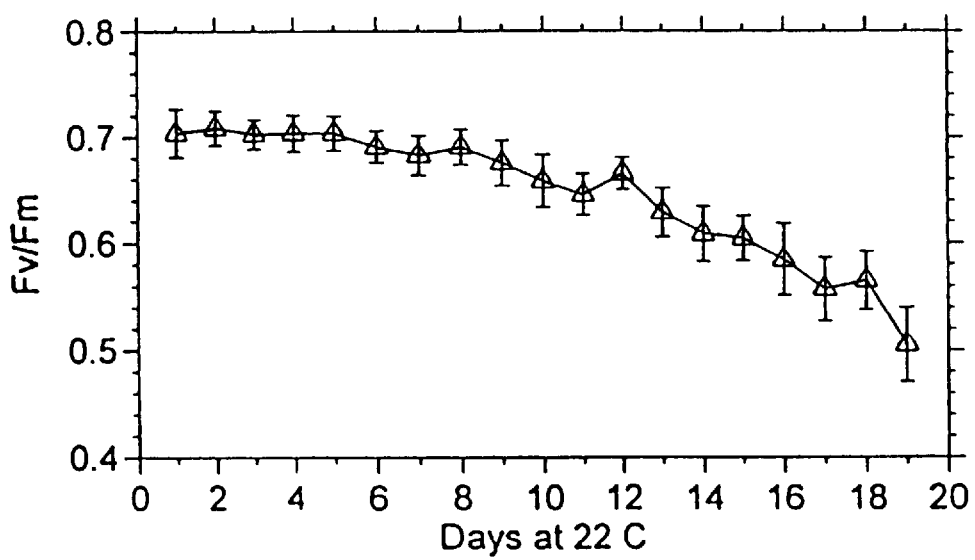
Figure 6:
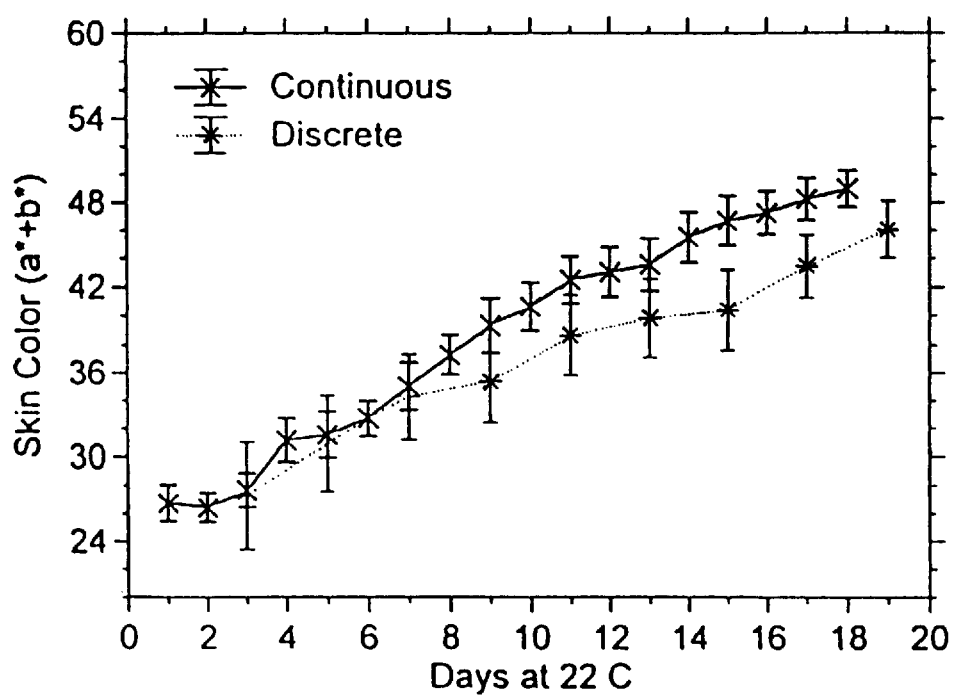
FIG. 6 is a graph showing changes in skin color of 'Golden Delicious' apple fruit at 22° C. in air following removal from CA storage (4.5 months, 1.5% $O_2$, <2.0% $CO_2$). Bars represents ±S.E.
Figure 7A:
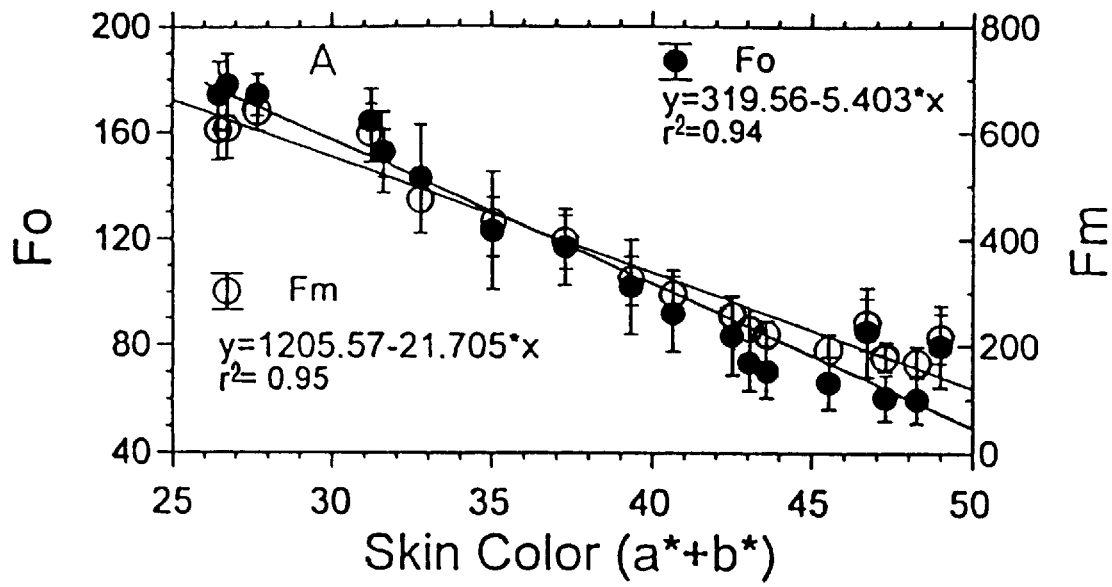
FIGS. 7A and 7B are graphs showing the relationship between fluorescence parameters (Fo and Fm) and skin color for continuous (A) and discrete (B) samples of 'Golden Delicious' apple fruit at 22° C. in air following removal from CA storage (4.5 months, 1.5% $O_2$, <2.0% $CO_2$). Lines represent best fit curvilinear equations.
Figure 7B:
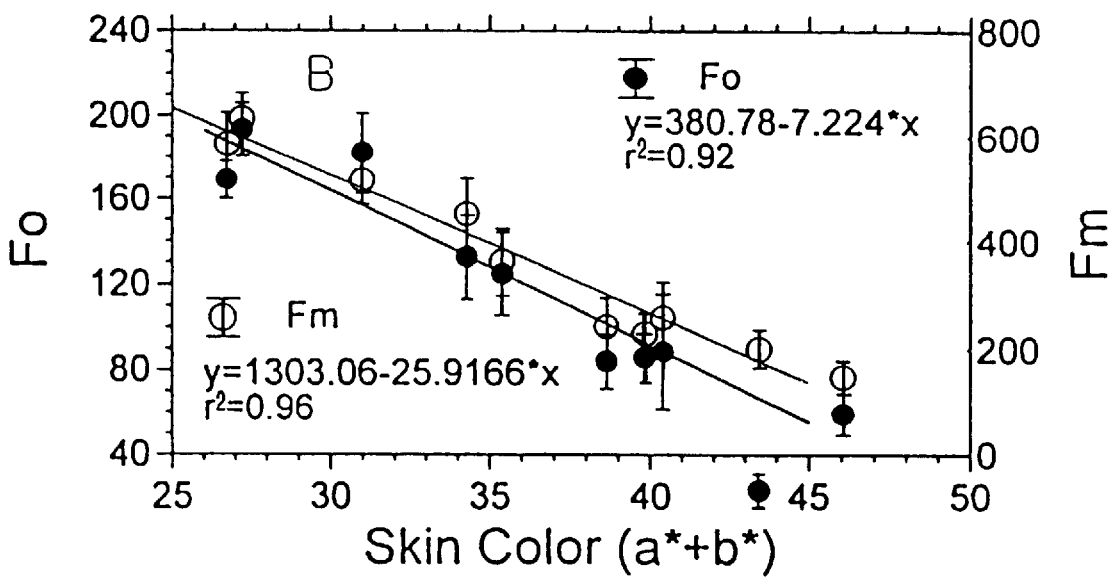
Figure 8A:
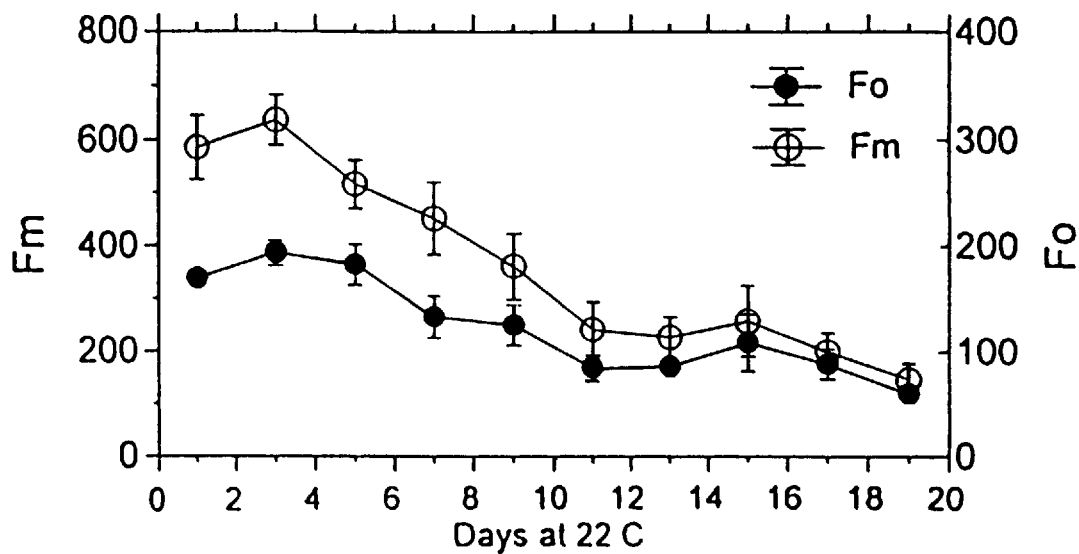
FIGS. 8A and 8B are graphs showing the decline in chloroplast fluorescence parameters of discrete samples for 'Golden Delicious' apple fruit at 22° C. in air following removal from CA storage (4.5 months 1.5% $O_2$, <2.0% $CO_2$). Each data point represents five fruit. Bar represents ±S.E.
Figure 8B:
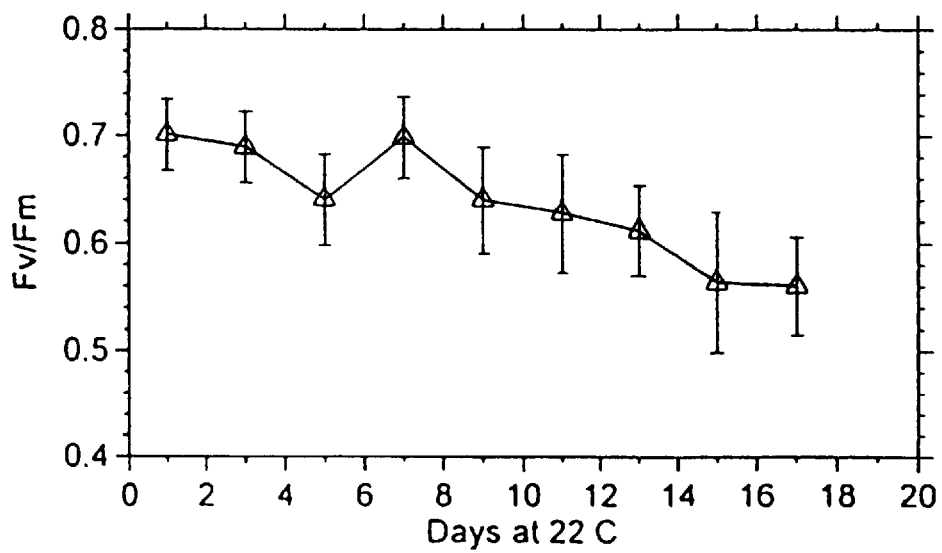

Post-storage chances in 'Golden Delicious'. The pattern of fluorescence changes for 'Golden Delicious' fruit were similar to those for 'Red Delicious'. In the continuous 'Golden Delicious' experiment, Fo and Fm decreased dramatically from 170 to 60 and 600 to 150, respectively, over the 18-day holding period (FIG. 5A). In contrast, Fv/Fm declined only slightly, going from 0.71 to 0.64 over the holding period (FIG. 5B). Skin color (a*+b*) increased from 25 to 48 as visible color changed from light green to full yellow (FIG. 6). Skin color was highly correlated with both Fm ($r^2$=0.95) and Fo ($r^2$=0.94) in a linear manner (FIG. 7A). In the discrete measurement fruit, the Fo, Fm and Fv/Fm decreased with time at 22° C. as it did for 'Golden Delicious' fruit in the continuous experiment (FIG. 8). Fruit firmness deceased only 5N from 57N to 52N (FIG. 3). Firmness changed with Fv/Fm in an apparently non-linear manner, having a correlation coefficient of 0.67 (Data not shown). Fruit skin color changes were similar in the continuous experiment (FIG. 6), being correlated with Fm ($r^2$=0.96) and Fo ($r^2$=0.92) in a linear manner (FIG. 7B).

Figure 9B:
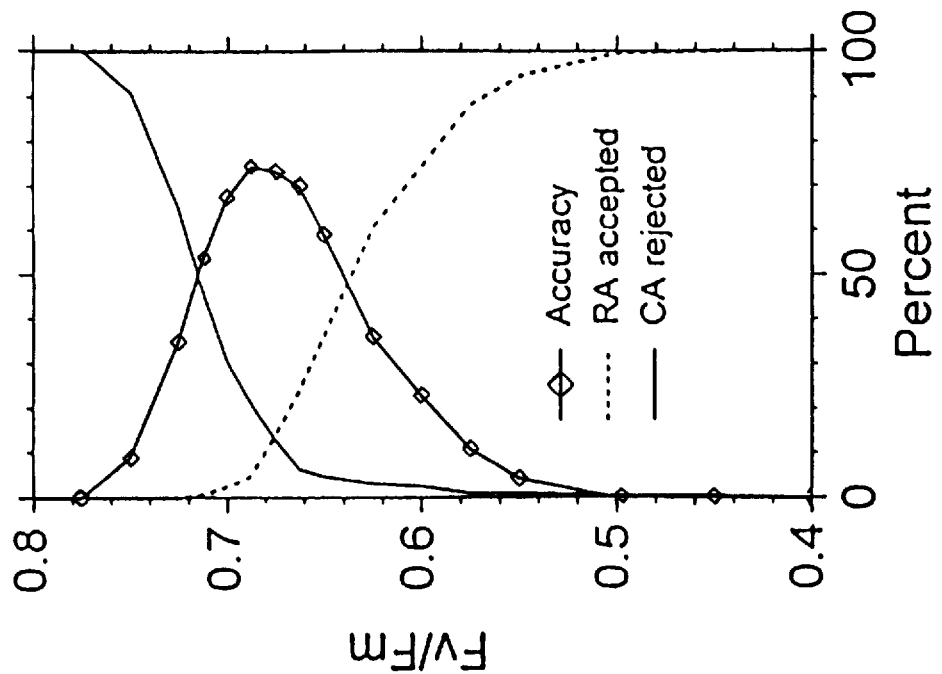
FIGS. 9A and 9B are graphs showing fluorescence (Fv/Fm) and MT-firmness for 'Law Rome' apple fruit from CA storage (1.5% $O_2$, <2.0% $CO_2$) and RA storage for 4.5 months (a) and segregation success using Fv/Fm threshold (b). Traces along Y-axis represent normalized frequency distributions of Fv/Fm for CA (solid line) and regular-air (RA) (dashed line) fruit.
Figure 9A:
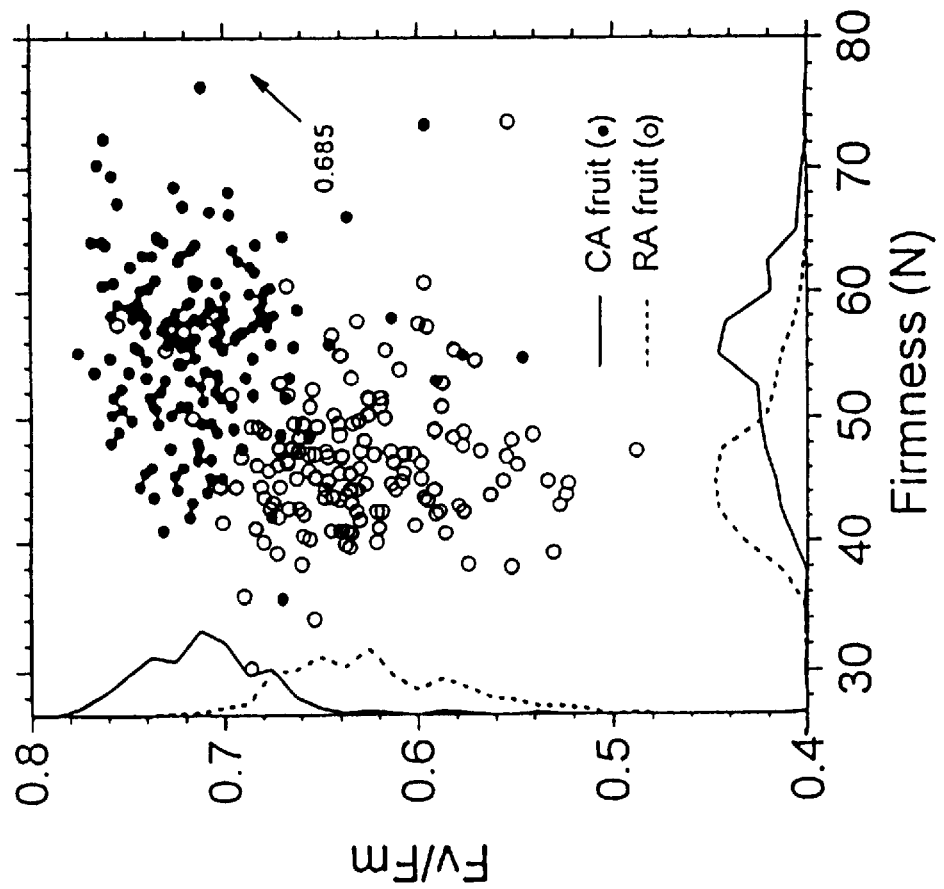

Sorting CA- and RA-sorted 'Law Rome'. Fluorescence, measured as Fv/Fm was regressed against firmness for high quality (CA-stored) and lost quality (RA-stored) fruit (FIG. 9A). The normalized frequency distributions of firmness (X-axis) and Fv/Fm (Y-axis) of the RA and CA fruit populations are depicted on the respective axes of FIG. 9A. The two populations appeared to segregate according to both firmness and Fv/Fm, but there was substantially less overlap in the frequency distribution for Fv/Fm than that of firmness. When Fv/Fm was used to segregate RA fruit from CA fruit, the ratio of the percentage of correct segregates (accuracy) was at a maximum (75%) at Fv/Fm=0.685 (FIG. 9B). At this threshold, approximately 5% of the poor quality fruit were wrongly categorized as high quality and approximately 20% of the high quality CA fruit were categorized as poor quality, RA-stored fruit. On the other hand, the greatest accuracy for a segregation based on firmness was only 55% when fruit softer than 49.5N were categorized as "RA-stored" and firmer fruit being classified as "CA-stored" (data not shown). The fluorescence of CA-stored 'Law Rome' fruit was not affected by the degree of skin coloration (data not shown). The decline in chloroplast function parallels the decline in more global aspects of plant organ senescence. For fruit, the decline in Fm, Fo or Fv/Fm can be used as an indicator of senescence of the whole fruit. Firmness, color and fruit flavor, which undergo time and temperature-dependent changes following harvest (Brackmann, A. J., et al., J. Amer. Soc. Hort. Sci. 118:243–247 (1993); Knee, M., et al., J. Hort. Sci. 64:403–411 (1989); Lau, O. L., Harvest indices for B. C. apples. B. C. Orchardist 7:1A–20A (1985); Lau, O. L., J. Amer. Soc. Hort. Sci. 113:564–569 (1988)) are accompanied by time and temperature-dependent changes in chloroplast function and capacity.

The loss in fruit greenness as fruits age is often used as an indicator of maturity and/or senescence (Kingston, C. M., Horticulture Review, 407–432 (1992); Lau, O. L., Harvest indices for B. C. apples. B. C. Orchardist 71A–20A (1985); Lau, O. L., J. Amer. Soc. Hort. Sci. 113:564–569 (1988)). The change in fruit color is a result of chlorophyll loss and, to a limited degree, carotenoid accumulation (Knee, M., J. Expt. Bot. 23:184–196 (1972)). In that Fo is a quantity that is dependent upon the amount of light chlorophyll emits under illumination that does not induce $O_2$ generation, Fo should reflect relative chlorophyll content. Thus, a loss in chlorophyll content exhibited as a loss in greenness should be correlated with Fo. The highly correlative relationship between 'Golden Delicious' fruit color and Fo is consistent with this. Although Fm is a reflection of both chlorophyll content and function, the strong correlations found between color and Fm also add support to the suggestion that fruit color (i.e., background color and fluorescence are related physiologically. This supposition is consistent with the findings of Smillie, R. M., et al Asean Fd. J. 3:55–59 (1987)), who reported fluorescence during ripening of banana and mango fruit at 20° C. as a result of loss in chlorophyll content and a decrease in photosynthetic competency per unit chlorophyll. Interestingly, fluorometry may offer a means of assessing background color on fruit with high levels of red pigmentation. Abbott, J. A., Nondestructive Techniques for Quality Evaluation of Fruits and Vegetables Amer. Soc. Ag. Engin., St. Joseph, Mich., ASAE 05-94 (1994)) commented that fluorescence measurements for predicting chilling injury in eggplant (Solanum melongena) were limited by high concentrations of pigments. However, the finding that the blush or red coloration of apple does not interfere with fluorescence readings suggests the same may not be true for apple.

The concept that fluorescence measurements can, to some extent, define the degree of fruit senescence is further strengthened by the highly correlative relationship of Fv/Fm to firmness. Fluorescence measurements are made from chlorophyll-containing tissue in the upper few cell layers, which are removed for firmness determination. If the decline in fluorescence were not synchronous with other aspects of tissue degradation such as tissue softening, then one would not necessarily expect a decline in firmness to correlate with a decline in chlorophyll fluorescence. However, in this work, firmness and fluorescence declined synchronously. This suggests that fluorescence parameters and textural factors are changing in response to similar or identical stimuli. The implication is that fluorescence may serve as a correlative measure of fruit firmness or fruit firmness retention and, perhaps, fruit condition or ability to retain condition.

The experiment using Fv/Fm to segregate CA- and air-stored fruit suggests the chloroplast fluorescence parameter Fv/Fm can be put to practical use by the fruit industry. The amount of fruit-to-fruit variation within a population is of some concern, however. The minimal 25% error rate reported here, while lower than that for firmness, may not be acceptable in an industry where low profit margins are typical. Use of this technology may rely on improving measurement techniques and/or sorting algorithms that take into account more than one fluorescence parameter. Alternatively, coupling fluorescence equipment with another, complimentary, non-destructive technology might be helpful.

The findings relating fluorescence and firmness and background color for 'Red Delicious', 'Golden Delicious' and 'Law Rome' fruit give rise to the possibility that chloroplast fluorescence can be used as a practical tool to estimate fruit condition.

Alternatively, fluorescence may have potential to be used as a measure of fruit injury or stress during the postharvest period, as induced by conditions of low $O_2$ or elevated $CO_2$ (DeEll, J. R., et al., HortScience 30:782 (1995)) or disorder development (Beaudry, R. M., et al., HortScience 30:816 (1995); Woolf, A. B., and W. A. Laing, J. Amer. Soc. Hort. Sci. 121:147–151 (1996)). However, a number of issues have yet to be resolved regarding the use of fluorescence for condition assessment. Cultivar, temperature, and storage atmosphere effects on the relationship between chlorophyll fluorescence and firmness, mealiness, flavor, etc., need to be determined. Furthermore, physically accomplishing the task of fluorescence measurement in the timescale needed to sort apple fruit may pose a challenge. Although fluorescence parameters can be collected within 1 sec per fruit, fruit throughput on packinglines is usually to 10 fruit/sec, perhaps the use of multi-line detectors, sensing (and sorting) may be an option. Despite these difficulties fluorescence has good potential to provide information needed to assist size and color sorting systems in obtaining a higher quality, more competitively positioned packout for apple fruit.

EXAMPLE 2

The relationship between Fv/Fm and freshly harvested peaches was examined. Fruit were harvested from trees at the Southwest Michigan Research and Education Center of Michigan State University in August of 1995. A very good correlation was obtained between fruit firmness and the fluorescence parameter Fv/Fm (FIG. 10).

EXAMPLE 3

In another study on 'Red Delicious' apple fruit, we tried to ascertain to what degree fluorescence changes with fruit maturity and storage duration and to determine if fluorescence may be related to fruit quality as an indicator of storage scald development. 'Red Delicious' is one of the more scald susceptible cultivars. The development of scald was scanned in the same lots of fruit at 7th days after removal from storage.

Materials and Methods

Apple fruit (Malus domestica Borkh 'Red Delicious') were harvested at twelve maturities for determining the effect of harvest date/maturity on fluorescence and at three maturities (Oct. 7, Oct. 14 and Oct. 21) for the storage experiment. Fruit were stored at week, then placed at ambient temperature (22° C.). Chloroplast fluorescence (quantum yield response; Fv/Fm) was measured at 0, third and 7th day after removal, the scald index was investigated at the 7th day after removal at 22° C.

Chlorophyll fluorescence. Fluorescence measurements were made in a dark laboratory as described previously (Beaudry, R. M., et al., HortScience 30:816 (1996)).

Scald development. Scald development was recorded as percent incidence.

MT Firmness. The firmness of fruit was conducted manually using a drill-stand-mounted Effegi penetrometer as described by Beaudry et al. (HortScience 30:816 (1996)).

Results

Fruit maturity. Fluorescence appears to be affected by fruit maturity (FIG. 11). The later harvest fruit had a lower Fv/fm, as well as lower Fm (data not shown), meaning that chlorophyll fluorescence is a ripening or senescence related factor in apple fruit. During ripening, the decrease in Fm and Fv/Fm may be caused by the breakdown of PSII center and slowdown of energy output from the PSII, which coincides with earlier findings by Beaudry et al (HortScience 30:816 (1996)) in 'Golden Delicious' and 'Red Delicious' at 20° C. in air following removal from the CA storage. It seems that the changes in the thylakoid membranes resulting in a decrease quantitative yield of photosystem II which are involving the senescence of apple fruits.

Changes in Fo/Fm during the storage. A decline in Fv/Fm (quantum yield response), which indicates a reduction of chloroplast function. Fv/Fm was recorded after 30 days for the first harvest fruit (FIG. 12A), and 40–50 days for the second and third harvest fruit (FIGS. 12B, 12C). After 4 months storage, the Fv/Fm decreased about 30–40%. The decline in Fv/Fm preceded scald development by approximately 30 days for the first harvest fruits and 20–30 days for the second and third harvest fruits.

Scald development during storage. Scald development began at about 90 days after harvest and reached 50% of scald index at 155 days from the first harvest apples and 170 days from the second harvest apples (FIGS. 12A and 12B). At the end of storage, there were 80% and 62% scald in these harvest fruits. FIGS. 12A and 12B interpreted a close relationship with decline of Fv/Fm. As scald developed to about 50%, Fv/Fm were showed a similar range as 0.62 and 0.63 at first and second harvest fruits respectively (FIGS. 12A and 12B). The scald development in the third harvest fruit was significantly lower than other earlier harvest fruits, which shows a lower scald index of 30% and corresponded higher Fv/Fm level of 0.65 (FIG. 12C).

Watkins, C. B., et al., J. Amer. Soc. Hort. Sci. 120:88–94 (1995)) concluded that the superficial scald in 'Granny Smith' is a typical low temperature related disorder, which was induced by chilling and developed at warm temperature. However, there is no direct evidence to demonstrate the causal relationship between physiological status of chloroplast and scald development in apple fruit. It is interesting to note that the green part of fruit are more susceptible to scald, which has a high concentration of chlorophyll a and b. It seems important to study the relationship between chloroplast degradation scald development.

A number of physiological assays have been used to predict or measure chilling injury. Chlorophyll fluorescence analysis was discussed as a new tool for assessment of chilling injury (Wilson and Graves, Chilling Injury in Horticultural Crops, ed. C. Y. Wang (1990)).

Knee (Knee, M., J. Exper. Bot. 23:184–196 (1972)) reported that the degreening and yellow color development in apple fruit were caused by decrease in chlorophyll a and b as well as in β-carotene and an increase in mono-, and di-esters of xanthophyll. The formation of α-farnesene has been found mainly in chloroplast, therefore, it may be that the loss of β-carotene, may be a function of the accumulation of α-farnesene. These chloroplast-based changes in physiology should be detectable in the fluorescence activity of the apple fruit. However, the data suggest the relationship between scald development and fluorescence may be tenuous.

Interestingly, scalded tissue did not differ dramatically in fluorescence (Fv/Fm) despite marked browning of the tissues (Table 1). Even so, the decline in chloroplast fluorescence readings (Fm and Fv/Fm) took place significantly earlier than scald-symptom development. These results indicated that chloroplast fluorescence may be used as a predictive tool for scald development in stored apple fruits. The data suggest that fluorescence changes and scald development may be related physiologically.

It is clear that the senescence of chloroplast shares many general change of features, such as structure, composition and function. We are assuming that there are two possible reasons for the development of superficial scald in apple fruit; a: general induction by chilling; b: accumulation of toxic volatile compounds in cuticle at low temperature, which might be coming from the degradation of chloroplast. The identification of volatiles from chloroplast senescence in some apples and test of their toxicity to the apple tissue are still in progress.

TABLE 1

|  | Scald | Nonscald |
|---|---|---|
| FV/Fm | 0.6544 ± 0.061 | 0.6649 ± 0.061 |

*n = 10

EXAMPLE 4

Chloroplast fluorescence was used as a non-invasive probe to study senescence in refrigerated air-stored Golden Delicious apples.

The potential storage life of apples is closely associated with the maturity of the fruit at the time of harvest. No one measurement of apple maturity has been completely satisfactory, but fruit firmness has been a fairly reliable criterion when used on red delicious apples. However, considerable variation in the degree of maturation may occur among apples on the same tree and among apples from different trees in the same orchard. Moreover, the destructive nature of the firmness determination technique leaves us with no choice than to discard the fruit for which quality assessment has been established. In view of this, a non-destructive and rapid technique for assessing fruit quality for each fruit that actually reaches to the consumer is highly warranted.

During maturation, the external color of Golden Delicious apples changes from green to yellow. Conventionally, at harvest fruit of the entire range of color is segregated into green and yellow. The yellow and some of the less green fruit are marketed early for fresh consumption. The rest of the fruit which is green in color is held either until the color has changed from green to yellow or for long term storage. A standard protocol for predicting the storage life of Golden Delicious apples does not exist.

Materials and Methods

Golden Delicious (*Malus domestica* Borkh.) cultivar of apple was harvested from Horticulture Research Farm, Michigan State University, East Lansing, Mich. The fruits were divided into two lots. Lot one represented the fruits that were uniform in age, color, size and vigor. Lot two consisted of fruits that were uniform in age and size but differed in color. The color window selected in lot two allowed us to study fruits with chlorophyll concentration of 1.1 to 17.1 $\mu$g Chl $g^{-1}$ FW.

The fruits were stored for 2 months in refrigerated-air storage (4° C.) at the Department of Horticulture, Michigan State University. At the end of refrigerated air-storage, the fruit from both the lots were brought to the laboratory. Fruits of lot one were withheld at 23° C. for 22 days. Chlorophyll fluorescence on each individual fruit in lot 2 were determined and fruits were then sacrificed for chlorophyll analysis. A relationship between chlorophyll content and fluorescence components was developed. Seven fruits from lot one were ear-marked for studying daily changes in Chlorophyll Fluorescence at the same selected spots throughout the holding period. The purpose of the continuous measurement was to view changes in fluorescence parameters on the same fruit to reduce the effect of variation within a fruit population, thereby more clearly demonstrating changes in fluorescence with time. The remaining portion of the fruit from lot one was used for Chlorophyll and $O_2$ evolution measurements. During the holding period, fruit were kept at 23° C. in cardboard boxes under dark conditions to avoid moisture loss and light effects. All measurements were taken at 23° C. for chlorophyll fluorescence and chlorophyll content and 30° C. for $O_2$ evolution.

Chlorophyll fluorescence. Fluorescence measurements were made in a darkened laboratory as previously described. The quenching coefficients of Chlorophyll Fluorescence were calculated using the expressions given by Schreiber et al., (Schreiber, U., et al., Photosynth Res 10:51–62 (1986)).

Chlorophyll analysis. 0.5 g of peel discs (0.2 mm dia) from the peel portion that was earmarked for fluorescence measurements was immersed into N,N-Dimethylformamide to a final volume of 5 mL. The samples were stored overnight in the dark under refrigeration. Chlorophyll concentration in the filtered extract was determined as described by Mackinney (Mackinney, G., J. Biol. Chem. 140:315–322 (1941)).

Measurement of $O_2$ evolution from peel discs. Peel discs (0.2 mm dia) were immersed in a reaction medium that contained 330 mM Betaine and 50 mM Hepes-KOH buffer, pH adjusted to 7.6. $O_2$ evolution in the light or consumption in the dark were measured as described by Mir, N. A., et al. (Plant Physiol. 108:313–318 (1995)).

Artificial electron acceptors and inhibitors of photosynthetic electron transport chain. Artificial electron acceptors and/or inhibitors were vacuum infiltrated in the whole fruit to drain or inhibit electrons from photosynthetic electron transport chain. PSII acceptors, 2,6-dimethylbenzoquinone (500 $\mu$M plus ferricyanide and PSI acceptors, methyl viologen (1 mM) and N,N-dimethyl-p-nitrosoaniline (200 $\mu$M) were used to drain electrons from photosynthetic electron transport chain in whole fruit. The photosynthetic electron transport was blocked by vacuum infiltrating 3-(3,4-dichlorophenyl)-1,1-dimethylurea (50 $\mu$M) into the fruit.

Results

Post-storage Changes in Chlorophyll Fluorescence. Post-storage changes in Chlorophyll fluorescence parameters, $F_m$, $F_o$ and variable fluorescence quenching during air-storage are presented in FIG. 13. The maximum Chlorophyll fluorescence ($F_m$) was at its maximum value (1300) from 0 to 1 days of air-storage. The $F_m$ declined with storage time from day 1 to 18, the decline was rapid from day 3 to 14. The Fm remained at a steady state level after 18 days of storage. The minimal amount of fluorescence that is recorded in the dark ($F_o$) also declined with advancement of storage time, the rate of decline was maximal from day 9 to 15. The combined changes in $F_o$ and $F_m$ were reflected in the quenching pattern of variable fluorescence. The capacity of the photosynthetic system to quench variable fluorescence declined rapidly from day 4 through 9. Withholding fruit beyond 9 days under ambient conditions did not influence the amount and degree of fluorescence quenching in apple.

Post-storage changes in Chlorophyll content. Chlorophyll changes in the fruits during air-storage are shown in FIG. 14. The fruit had on an average Chlorophyll content of 10 $\mu$g g$^{-1}$ FW. The total Chlorophyll content of the fruit declined from day 0 through 18, it remained almost unchanged from day 18 to 21. While Chlorophyll a degradation was similar to total Chlorophyll degradation, Chlorophyll b declined more rapidly from day 9 through 12. The ratio of Chlorophyll a/b by and large, remained from 3.7 to 4 during entire period of storage. Knee (Knee, M., J. Exper. Bot. 23:184–196 (1972)) has shown that Chlorophyll a and Chlorophyll b degraded at a similar rate in 'Cox's Orange Pippin' during storage.

Post-storage changes in chloroplast activity. $O_2$ evolution from peel discs due to photosynthetic electron transport was used to determine the postharvest changes in chloroplast activity in vivo and are shown in FIG. 15. Under steady state photosynthesis conditions, peel discs evolved 15 $\mu$mol of $O_2$ g$^{-1}$ FW h$^{-1}$. The capacity of the peel discs to evolve $O_2$ in the medium declined gradually from day 0 through 18 during air-storage. Peel discs obtained from the fruit through day 18 to 21 failed to evolve any photosynthetic $O_2$ in the reaction medium.

Post-storage changes in the dark respiration. The dark respiratory consumption of $O_2$ stayed at a similar level up to 9 days of storage (FIG. 15). The rate of respiration increased linearly from day 9 through 15 and plateaued at 18 through 22 days of air-storage.

Relationship between Chlorophyll content and Fluorescence parameters of apple fruit. The fluorescence data that was collected form 71 randomly selected fruits in a Chlorophyll range of 1.1 to 17.1 $\mu$g g$^{-1}$ FW was regressed against fruit Chlorophyll content (FIG. 16). With the increase in fruit Chlorophyll concentration, the fluorescence parameters, $F_o$ and $F_m$ increased in a sigmoidal manner (FIG. 16). $F_o$ and $F_m$ were highly correlated with (Chlorophyll a+Chlorophyll b). While the variable fluorescence quenching also increased, the amount of fluorescence (1-$F_v$/$F_m$) decreased with increase in fruit (Chlorophyll) (FIG. 16). Using the empirical equations that were fitted for $F_o$ and $F_m$, $F_v$/$F_m$ as a function of Chlorophyll concentration in the fruit were predicted from the fitted curves which described the actual data reasonably well (FIG. 17).

Effect of artificial electron acceptors on variable fluorescence quenching in whole fruit. When the surface of apple was excited with a continuous light source of 2,000 $\mu$mol m$^{-2}$ s$^{-1}$, the fluorescence was quenched by 72% of $F_v$. Infiltration of artificial electron acceptors into the fruit that would accept electrons at PSII (DMQ) or PSI (PNDA) increased slightly the total electron capacity of the photosynthetic electron transport chain as judged by increase in fluorescence quenching over control. These results suggest that the capacity of the electron transport chain is not limited by the availability of the acceptors under in vivo conditions. The PSI electron acceptor, MV resulted in physical damage of the tissue which was more pronounced after 4 hours of infiltration. Addition of DCMU, 50 $\mu$M into the infiltration medium in presence or absence of artificial electron acceptors prevented the quenching of variable fluorescence in apple.

Discussion

Senescence has been defined as a process of deteriorative events which precede the death of mature cell (Beevers, L., Plant Biochemistry, J. Bonner and J. E. Varner (Eds), Academic Press, N.Y. p. 771–794 (1976)). According to this view, attached fruit that are close to the completion of their life span and detached fruit which represent induced termination of life activities might be assumed to follow similar physiology. In practice, apple fruit is harvested when it has attained a certain level of dessert quality, which makes it suitable for marketing or storage. Little or no attention is paid to the factors that determine fruit senescence, a process which dictates the post harvest life of the fruit. However, previous studies have indicated that fruits harvested at pre-climacteric stage of development have extended life of storage than fruits that are harvested at post-climacteric stage (Kingston, C. M., Horticulture Reviews, 407–432 (1992)).

Golden Delicious apples change color from green to yellow on maturation or in the storage. The color transformation window is relatively wider in comparison to the varieties which change from green to red like Red Delicious. This phenomenon helps one to have a close track of whole fruit senescence as well as chloroplast senescence during storage. For clarity, we mean by chloroplast senescence, fruit senescence-associated in vivo changes. It differs from chloroplast aging which on the other hand, indicates time dependent alterations in chloroplast under in vitro conditions.

In the photosynthetic apparatus, the light absorption by the antenna pigments results in transfer of excitation energy to the reaction centers of two photosystems, PSII and PSI. Consequently, the primary well known photochemical reactions are initiated to converse this energy into various chemical forms. At low light, the yield of photochemical energy conversion in a photosynthetic system is way higher than high light. (Bjorkman, O., and B. Dammig, Planta 170:489–504 (1987)). The amount of energy that is not conversed by the photosynthetic system is emitted as fluorescence, a reaction that results in deactivation of excited chlorophyll molecules.

Apple leaves or fruit display maximum Chlorophyll Fluorescence ($F_m$) when the electron transport from $Q_A$ to $Q_B$ is blocked by DCMU (FIG. 18). The $F_m$ can also be obtained, if the plastoquinone pool in the photosynthetic electron transport chain is reduced completely with a saturating flash of light (FIGS. 13, 18). This maximal Chlorophyll F is quenched by 80% of $F_v$, if the photosynthetic fixation of $CO_2$ is allowed (FIG. 13). This maximal Fluorescence is also quenched in large amounts when the capacity of the photosynthetic system to fix $CO_2$ had been practically lost (lack of $O_2$ evolution; after 18 days of air-storage, FIG. 15). As in leaves of apple (data not shown) and other vascular plants, variable fluorescence quenching in whole fruit has two components, the large photochemical (79.55%) and small non-photochemical (20.45%) quenching.

During senescence, the quality of apple fruit with regard to color, texture and flavor change dramatically. There is a general agreement that membrane deterioration (Meir, S., et al., Postharvest Biol. Tech. 2:125–135 (1992)) resulting in fruit softening (Dull, G. G., and A. C. Hulm, Quality, In: A. C. Hulme (ed.) The biochemistry of fruit and their products. Vol. 2 Academic Press London and New York 721–725 (1971)) is a fundamental aspect of fruit senescence. While the chloroplast membranes retain their physical integrity until late in senescence, photosynthetic capacity declines from the earliest stages of senescence (Gepstein, S., Photosynthesis In: L. D. Nooden and A. C. Leopold (eds.) Senescence and aging in plants. Academic Press, NY. p. 85–109 (1988)). In these experiments we used chlorophyll a fluorescence parameters, $F_o$ and $F_m$ as index of photosynthetic pigment complex (FIGS. 13, 16). Quantitative determinations of Chlorophyll over time were also made (FIGS. 14, 16). The fluorescence parameters, $F_o$ and $F_m$ declined rapidly during first two weeks of storage (FIG. 13). Since $F_o$ and $F_m$ represent the Chlorophyll a concentration in the fruit, a similar pattern as can be seen in $F_o$ or $F_m$ was observed in Chlorophyll a degradation (FIG. 14). The degradation of Chlorophyll b, by and large, followed Chlorophyll a almost closely maintaining a Chlorophyll a/Chlorophyll b ratio of 3.7 to 4 during entire period of storage (FIG. 14). This pattern is somewhat different from leaves where marked differences in degradation rates of Chlorophyll a and Chlorophyll b during senescence are observed (Grover, et al., In Photosynthesis: photoreactions to plant productivity, eds. Y. P. Abrol, P. Mohanty, Govindjee, 226–255 (1992); Kura-Hotta et al., Plant and Cell Physiol 28(7): 1321–1329 (1987)). To test the physiological state of the chloroplasts during senescence, were used two approaches were used. Approach 1 consisted of measurements of variable fluorescence quenching in whole fruit over time and approach 2 was quantification of photosynthetic $O_2$ evolution due to photolysis of $H_2O$ at PSII (FIG. 15). The variable fluorescence quenching declined from 78% to 71% of $F_v$ during air-storage. While the $O_2$ evolution due to $CO_2$ fixation also declined over time, it stopped completely in 3rd week of storage (FIG. 15). If the fluorescence quenching is only due to $CO_2$ fixation then one would expect no fluorescence quenching (FIG. 1) once no net $O_2$ evolution is seen from the apple chloroplasts (FIG. 15). However, it has been shown that the total electron generation as can be calculated (4 electrons for every $O_2$ mol evolved) from net $O_2$ may underestimate the total capacity of photosynthetic electron transport due to many potential pathways of $O_2$ metabolism in biological systems, pseudocyclic photophosphorylation being the predominant one (Sultemeyer, D. K., et al., Planta 189:235–242 (1993); Mir, N. A., et al., Plant Physiol. 109:1295–1300 (1995)). Interestingly, when DCMU which blocks electron transport at $Q_A$ to $Q_B$ was added to the senescent fruits, no quenching of variable fluorescence was observed. When this reaction was blocked by DCMU infiltration into the whole fruit (FIG. 18), quenching of variable fluorescence was prevented.

In the following claims, "modulation" refers to the fact that high frequency change in excitation light intensity is used and a detection system is used that can detect the high frequency changes in signal associated with the modulated light, the modulated light can be subtracted away from background interference, thereby reducing noise.

It is intended that the foregoing description be only illustrative of the present invention and that the present invention be limited only by the hereinafter appended claims.

We claim:

1. A method for indirectly estimating quality of a harvested, edible fruit or vegetable having a skin which comprises:
    (a) exposing the skin of the fruit or vegetable to a source of red light which induces a fluorescence intensity at a frequency above the red light from chlorophyll in the skin of the fruit or vegetable;
    (b) detecting the fluorescence intensity produced by the skin; and
    (c) estimating the quality of the fruit or vegetable as a function of the intensity of the fluorescence detected, wherein when the fruit or vegetable has a first level of the fluorescence of the chlorophyll in the skin when the fluorescence intensity is relatively high which is indicative of an acceptable quality and wherein the intensity of the fluorescence of the chlorophyll at a second level which is decreased and which is indicative of an unacceptable quality.

2. The method of claim 1 wherein the quality is selected from the group consisting of firmness, texture, color and aroma.

3. The method of claim 1 wherein the red light wavelength is at least about 690 nm and the fluorescence intensity is measured at wavelengths between about 710 and 740 nm.

4. The method of claim 1 wherein the source of the red light is part of a spectrum of a white light.

5. The method of claim 1 wherein the source of light is monochromatic.

6. The method of claim 5 wherein the light source generates a pulse of light.

7. The method of claim 1 wherein the source of light is continuous.

8. The method of claim 1 wherein the source of light is modulated.

9. A method for indirectly estimating quality of a fruit or vegetable having a skip which comprises:
    (a) exposing the skin of the fruit or vegetable to an applied continuous first source of light including red light which induces a background fluorescence intensity ($F_o$) and to a second source of light which provides a maximal fluorescence intensity ($F_m$) from the skin of the fruit or vegetable at longer wavelengths than the first light source;
    (b) detecting the fluorescence intensities $F_o$ and $F_m$ produced by the skin;
    (c) determining a fluorescence intensity ratio of $$\frac{F_m - F_o}{F_m}$$

wherein $F_m - F_o$ Fo is equal to a variable fluorescence intensity $F_v$; and
    (d) estimating the firmness of the fruit or vegetable as a function of the ratio, wherein the fruit or vegetable which has a first level of the chlorophyll in the skin as determined by the fluorescence intensity ratio has an acceptable quality and wherein the florescence intensity ratio is at a second level which is decreased and which is indicative of an unacceptable quality.

10. The method of claim 9 wherein the red light is at 690 nm and the fluorescence intensity is measured at about 710 to 740 nm.

11. The method of claim 9 wherein the quality is selected from the groups consisting of firmness, texture, color and aroma.

12. The method of claim 9 wherein the fruit is a red fruit.

13. An apparatus for indirectly estimating quality of a harvested, edible fruit or vegetable which comprises:
   (a) light source means for exposing the fruit or vegetable to a red light which induces a fluorescence intensity at a wavelength greater than that of the red light from the skin of the fruit or vegetable;
   (b) detection means for detecting the fluorescence intensity from the fruit or vegetable; and
   (c) calculator means for converting the intensity of the fluorescence into a measure of the quality of the fruit or vegetable, wherein the fruit or vegetable which has a first level of chlorophyll in the skin as determined by the fluorescence intensity which is indicative of an acceptable quality and wherein the fluorescence intensity is at a second level which is decreased and which is indicative of an unacceptable quality.

14. The apparatus of claim 13 wherein the calculator means is a computer.

15. The apparatus of any one of claims 13 or 14 wherein the light source means and detection means are mounted adjacent to a conveyor for the fruit or vegetable.

16. The apparatus of claim 13 wherein the quality is selected from the group consisting of firmness, texture, color and aroma.

17. The apparatus of claim 13 wherein the wavelength red light is at least about 690 nm and the fluorescence intensity is measured at wavelengths between about 710 and 740 nm.

18. The apparatus of claim 13 wherein the source of the red light is in a spectrum of white light.

19. The apparatus of claim 13 wherein the source of the red light is monochromatic.

20. The apparatus of claim 13 wherein the light source produces a light pulse.

21. The apparatus of claim 13 wherein the light source produces a continuous light.

22. An apparatus for estimating quality of fruit or vegetable having a skin which comprises:
   (a) a first light source of red light which is modulated and is a monochromatic;
   (b) a second light source which is continuous and produces an actinic light including red light;
   (c) fiber optic means comprising individual fibers in a bundle of a group of fibers with one end in a spaced apart relationship with a fruit or vegetable, wherein a first of the group of the fibers are illuminated by the second light source to provide the actinic light at the one end and on the fruit or vegetable, a second of the group of the fibers which are periodically illuminated by the first light source to provide the modulated and monochromatic light at the one end and on the fruit or vegetable and a third of the group of the fibers which directs fluorescent light from the fruit or vegetable produced by each of the first or second light sources at the one end; and
   (d) detection means connected to the third group of the fibers with circuit means for determining a first fluorescence intensity ($F_o$) produced by the second light source and for determining a fluorescence intensity ($F_m$) produced by the first light source for calculating a fluorescence intensity ratio of $$\frac{F_m - F_o}{F_m}$$

which when $F_m - F_o$ is equal to a variable fluorescence intensity ($F_v$), wherein the fruit or vegetable has chlorophyll in the skin as determined by the fluorescence intensity ratio which is at a first level indicative of an acceptable quality and wherein the fluorescence intensity ratio is at a second level which is decreased and which is indicative of an unacceptable quality.

23. The apparatus of claim 22 wherein the red light wavelength is at about 690 nm and the fluorescence intensity is measured at wavelengths in the range of 710 to 740 nm.

24. The apparatus of claim 22 wherein the quality is selected from the group consisting of firmness, texture, color and aroma.

* * * * *

UNITED STATES PATENT AND TRADEMARK OFFICE
CERTIFICATE OF CORRECTION

PATENT NO. : 5,822,068
DATED : October 13, 1998
INVENTOR(S) : Beaudry et al.

It is certified that error appears in the above-identified patent and that said Letters Patent is hereby corrected as shown below:

Column 9, line 41, "chances" should be --changes--.

Column 12, line 6, "stored at week" should be --stored for a week--.

Column 15, line 52, "collected form" should be --collected from--.

Column 17, line 37, "were used", first occurrence" should be deleted.

Column 18, line 40 (Claim 9), "skip" should be --skin--.

Column 18, line 55, "$F_m-F_0$ FO is equal" should be --$F_m-F_0$ is equal--.

Signed and Sealed this

Third Day of August, 1999

Attest:

Q. TODD DICKINSON

Attesting Officer

Acting Commissioner of Patents and Trademarks